United States Patent
Ashrafi et al.

(10) Patent No.: US 9,662,019 B2
(45) Date of Patent: May 30, 2017

(54) ORBITAL ANGULAR MOMENTUM AND FLUORESCENCE-BASED MICROENDOSCOPE SPECTROSCOPY FOR CANCER DIAGNOSIS

(71) Applicants: Solyman Ashrafi, Plano, TX (US); Roger Linquist, Dallas, TX (US); Nima Ashrafi, Plano, TX (US)

(72) Inventors: Solyman Ashrafi, Plano, TX (US); Roger Linquist, Dallas, TX (US); Nima Ashrafi, Plano, TX (US)

(73) Assignee: NXGEN PARTNERS IP, LLC, Dallas, TX (US)

( * ) Notice: Subject to any disclaimer, the term of this patent is extended or adjusted under 35 U.S.C. 154(b) by 212 days.

(21) Appl. No.: 14/681,683

(22) Filed: Apr. 8, 2015

(65) Prior Publication Data

US 2015/0289766 A1    Oct. 15, 2015

Related U.S. Application Data

(60) Provisional application No. 61/977,456, filed on Apr. 9, 2014.

(51) Int. Cl.
    *A61B 5/00*    (2006.01)
(52) U.S. Cl.
    CPC .......... *A61B 5/0084* (2013.01); *A61B 5/0035* (2013.01); *A61B 5/0071* (2013.01); *A61B 5/7282* (2013.01)
(58) Field of Classification Search
    CPC ... A61B 5/0059–5/0091; A61B 5/1455; A61B 5/14558; A61B 5/1459; A61B 5/418; A61B 5/4312; A61B 5/7282; A61B 1/005–1/07; A61B 1/00002–1/00062
    See application file for complete search history.

(56) References Cited

U.S. PATENT DOCUMENTS

| | | |
|---|---|---|
| 3,459,466 A | 8/1969 | Giordmaine |
| 3,614,722 A | 10/1971 | Jones |
| 4,379,409 A | 4/1983 | Primbsch et al. |
| 4,503,336 A | 3/1985 | Hutchin et al. |
| 4,736,463 A | 4/1988 | Chavez |
| 4,862,115 A | 8/1989 | Lee et al. |
| 5,051,754 A | 9/1991 | Newberg |
| 5,220,163 A | 6/1993 | Toughlian et al. |

(Continued)

OTHER PUBLICATIONS

Solyman Ashrafi, Channeling Radiation of Electrons in Crystal Lattices, Essays on Classical and Quantum Dynamics, Gordon and Breach Science Publishers, 1991.

(Continued)

*Primary Examiner* — Scott Getzow
(74) *Attorney, Agent, or Firm* — Howison & Arnott, LLP

(57) ABSTRACT

An apparatus for performing an endoscopic procedure for detecting cancerous tissue includes a detection probe for detecting the cancerous tissue. The detection probe includes a first fiber for emitting an ultraviolet light beam having an orthogonal function applied thereto and a second fiber for receiving emissions from tissues responsive to the ultraviolet light beam emitted for the first fiber. An ultraviolet emission source generates the ultraviolet light beam. Orthogonal function circuitry applies the orthogonal function twist to the ultraviolet light beam. Detection circuitry detects fluorescence and orthogonal function within the emissions from the tissues received over the second fiber.

30 Claims, 10 Drawing Sheets

(56) References Cited

U.S. PATENT DOCUMENTS

| | | |
|---|---|---|
| 5,222,071 A | 6/1993 | Pezeshki et al. |
| 5,272,484 A | 12/1993 | Labaar |
| 5,543,805 A | 8/1996 | Thaniyavarn |
| 5,555,530 A | 9/1996 | Meehan |
| 6,337,659 B1 | 1/2002 | Kim |
| 6,992,829 B1 | 1/2006 | Jennings et al. |
| 7,515,265 B2 | 4/2009 | Alfano et al. |
| 7,577,165 B1 | 8/2009 | Barrett |
| 7,729,572 B1 | 6/2010 | Pepper et al. |
| 7,792,431 B2 | 9/2010 | Jennings et al. |
| 8,432,884 B1 | 4/2013 | Ashrafi |
| 8,503,546 B1 | 8/2013 | Ashrafi |
| 8,559,823 B2 | 10/2013 | Izadpanah et al. |
| 8,811,366 B2 | 8/2014 | Ashrafi |
| 9,077,577 B1 | 7/2015 | Ashrafi |
| 2003/0191368 A1 | 10/2003 | Wang et al. |
| 2004/0010375 A1 | 1/2004 | Schomacker et al. |
| 2005/0254826 A1 | 11/2005 | Jennings et al. |
| 2005/0259914 A1 | 11/2005 | Padgett et al. |
| 2008/0294105 A1 | 11/2008 | Gono et al. |
| 2010/0013696 A1 | 1/2010 | Schmitt et al. |
| 2011/0137126 A1 | 6/2011 | French et al. |
| 2012/0207470 A1 | 8/2012 | Djordevic et al. |
| 2013/0027774 A1 | 1/2013 | Bovino et al. |
| 2013/0200895 A1 | 8/2013 | Van Der Brink |
| 2013/0235744 A1 | 9/2013 | Chen et al. |
| 2014/0355624 A1 | 12/2014 | Li et al. |
| 2015/0098697 A1 | 4/2015 | Marom et al. |

OTHER PUBLICATIONS

Solyman Ashrafi, Solar Flux Forecasting Using Mutual Information with an Optimal Delay, Advances in the Astronautical Sciences, American Astronautical Society, vol. 84 Part II, 1993.

Solyman Ashrafi, PCS system design issues in the presence of microwave OFS, Electromagnetic Wave Interactions, Series on Stability, Vibration and Control of Systems, World Scientific, Jan. 1996.

Solyman Ashrafi, Performance Metrics and Design Parameters for an FSO Communications Link Based on Multiplexing of Multiple Orbital-Angular-Momentum Beams, Globecom2014 OWC Workshop, 2014.

Solyman Ashrafi, Optical Communications Using Orbital Angular Momentum Beams, Adv. Opt. Photon. 7, 66-106, Advances in Optics and Photonic, 2015.

Solyman Ashrafi, Performance Enhancement of an Orbital-Angular-Momentum-Based Free-Space Optical Communication Link through Beam Divergence Controlling, OSA Technical Digest (online), paper M2F.6. The Optical Society, 2015.

Solyman Ashrafi, Experimental demonstration of enhanced spectral efficiency of 1.18 symbols/s/Hz using multiple-layer-overlay modulation for QPSK over a 14-km fiber link. OSA Technical Digest (online), paper JTh2A.63. The Optical Society, 2014.

Solyman Ashrafi, Link Analysis of Using Hermite-Gaussian Modes for Transmitting Multiple Channels in a Free-Space Optical Communication System, The Optical Society, vol. 2, No. 4, Apr. 2015.

Solyman Ashrafi, Performance Metrics and Design Considerations for a Free-Space Optical Orbital-Angular-Momentum-Multiplexed Communication Link, The Optical Society, vol. 2, No. 4, Apr. 2015.

Solyman Ashrafi, Demonstration of Distance Emulation for an Orbital-Angular-Momentum Beam. OSA Technical Digest (online), paper STh1F.6. The Optical Society, 2015.

Solyman Ashrafi, Free-Space Optical Communications Using Orbital-Angular-Momentum Multiplexing Combined with MIMO-Based Spatial Multiplexing. Optics Letters, vol. 40, No. 18, Sep. 4, 2015.

Solyman Ashrafi, Enhanced Spectral Efficiency of 2.36 bits/s/Hz Using Multiple Layer Overlay Modulation for QPSK over a 14-km Single Mode Fiber Link. OSA Technical Digest (online), paper SW1M.6. The Optical Society, 2015.

Solyman Ashrafi, Experimental Demonstration of a 400-Gbit/s Free Space Optical Link Using Multiple Orbital-Angular-Momentum Beams with Higher Order Radial Indices. OSA Technical Digest (online), paper SW4M.5. The Optical Society, 2015.

Solyman Ashrafi, Experimental Demonstration of 16-Gbit/s Millimeter-Wave Communications Link using Thin Metamaterial Plates to Generate Data-Carrying Orbital-Angular-Momentum Beams, ICC 2015, London, UK, 2014.

Solyman Ashrafi, Experimental Demonstration of Using Multi-Layer-Overlay Technique for Increasing Spectral Efficiency to 1.18 bits/s/Hz in a 3 Gbit/s Signal over 4-km Multimode Fiber. OSA Technical Digest (online), paper JTh2A.63. The Optical Society, 2015.

Solyman Ashrafi, Experimental Measurements of Multipath-Induced Intra- and Inter-Channel Crosstalk Effects in a Millimeter-Wave Communications Link using Orbital-Angular-Momentum Multiplexing, ICC 2015, London, UK, 2014.

Solyman Ashrafi, Performance Metrics for a Free-Space Communication Link Based on Multiplexing of Multiple Orbital Angular Momentum Beams with Higher Order Radial Indice. OSA Technical Digest (online), paper JTh2A.62. The Optical Society, 2015.

Solyman Ashrafi, 400-Gbit/s Free-Space Optical Communications Link Over 120-meter Using Multiplexing of 4 Collocated Orbital-Angular-Momentum Beams. OSA Technical Digest (online), paper M2F.1. The Optical Society, 2015.

Solyman Ashrafi, Experimental Demonstration of Two-Mode 16-Gbit/s Free-Space mm-Wave Communications Link Using Thin Metamaterial Plates to Generate Orbital Angular Momentum Beams, Optica, vol. 1, No. 6, Dec. 2014.

Solyman Ashrafi, Demonstration of an Obstruction-Tolerant Millimeter-Wave Free-Space Communications Link of Two 1-Gbaud 16-QAM Channels using Bessel Beams Containing Orbital Angular Momentum, Third International Conference on Optical Angular Momentum (ICOAM), Aug. 4-7, 2015, New York USA.

Wang et al: "Terabit free-space data transmission employing orbital angular momentum multiplexing", Nature Photonics, vol. 6, Jul. 2012, pp. 488-496.

Solyman Ashrafi, An Information Theoretic Framework to Increase Spectral Efficiency, IEEE Transactions on Information Theory, vol. XX, No. Y, Oct. 2014, Dallas, Texas.

H. Yao et al, Patch Antenna Array for the Generation of Millimeter-wave Hermite-Gaussian Beams, IEEE Antennas and Wireless Propagation Letters, (pending publication), (2017).

Yongxiong Ren et al, Experimental Investigation of Data Transmission Over a Graded-index Multimode Fiber Using the Basis of Orbital Angular Momentum Modes (pending publication), (2017).

M. Nouri et al., Perturbations of Laguerre-Gaussian Beams by Chiral Molecules (pending publication), (2017).

Solyman Ashrafi, Acoustically induced stresses in elastic cylinders and their visualization, The Journal of the Acoustical Society of America 82(4):1378-1385, Sep. 1987.

Solyman Ashrafi, Splitting of channeling-radiation peaks in strained-layer superlattices, Journal of the Optical Society of America B 8(12), Nov. 1991.

Solyman Ashrafi, Spurious Resonances and Modelling of Composite Resonators, 37th Annual Symposium on Frequency Control, 1983.

Solyman Ashrafi, Splitting and contrary motion of coherent bremsstrahlung peaks in strained-layer superlattices, Journal of Applied Physics 70:4190-4193, Dec. 1990.

Solyman Ashrafi, Evidence of Chaotic Pattern in Solar Flux Through a Reproducible Sequence of Period-Doubling-Type Bifurcations, Proceedings of Flight Mechanics/Estimation Theory Symposium, National Aeronautics and Space Administration, May 1991.

Solyman Ashrafi, Combining Schatten's Solar Activity Prediction Model with a Chaotic Prediction Model, National Aeronautics and Space Administration, Nov. 1991.

Solyman Ashrafi, Nonlinear Techniques for Forecasting Solar Activity Directly From its Time Series, Proceedings of Flight Mechanics/Estimation Theory Symposium, National Aeronautics and Space Administration, May 1992.

(56) References Cited

OTHER PUBLICATIONS

Solyman Ashrafi, Detecting and Disentangling Nonlinear Structure from Solar Flux Time Series, 43rd Congress of the International Astronautical Federation, Aug. 1992.

Solyman Ashrafi, Physical Phaseplate for the Generation of a Millimeter-Wave Hermite-Gaussian Beam, IEEE Antennas and Wireless Propagation Letters, RWS 2016; pp. 234-237.

Solyman Ashrafi; Future Mission Studies: Preliminary Comparisons of Solar Flux Models; NASA Goddard Space Flight Center Flight Dynamics Division; Flight Dynamics Division Code 550; Greenbelt, Maryland; Dec. 1991.

Ren, Y. et al.; Experimental Demonstration of 16 Gbit/s millimeter-wave Communications using MIMO Processing of 2 OAM Modes on Each of Two Transmitter/Receiver Antenna Apertures. In Proc. IEEE GLobal TElecom. Conf. 3821-3826 (2014).

Li, X. et al.; Investigation of interference in multiple-input multiple-output wireless transmission at W band for an optical wireless integration system. Optics Letters 38, 742-744 (2013).

Padgett, Miles J. et al., Divergence of an orbital-angular-momentum-carrying beam upon propagation. New Journal of Physics 17, 023011 (2015).

Mahmouli, F.E. & Walker, D. 4-Gbps Uncompressed Video Transmission over a 60-GHz Orbital Angular Momentum wireless Channel. IEEE Wireless Communications Letters, vol. 2, No. 2, 223-226 (Apr. 2013).

Vasnetsov, M. V., Pasko, V.A. & Soskin, M.S.; Analysis of orbital angular momentum of a misaligned optical beam; New Journal of Physics 7, 46 (2005).

Byun, S.H., Haji, G.A. & Young, L.E.; Development and application of GPS signal multipath simulator; Radio Science, vol. 37, No. 6, 1098 (2002).

Tamburini, Fabrizio; Encoding many channels on the same frequency through radio vorticity: first experimental test; New Journal of Physics 14, 033001 (2012).

Gibson, G. et al., Free-space information transfer using light beans carrying orbital angular momentum; Optical Express 12, 5448-5456 (2004).

Yan, Y. et al.; High-capacity millimetre-wave communications with orbital angular momentum multiplexing; Nature Communications; 5, 4876 (2014).

Hur, Sooyoung et at.; Millimeter Wave Beamforming for Wireless Backhaul and Access in Small Cell Networks. IEEE Transactions on Communications, vol. 61, 4391-4402 (2013).

Allen, L., Beijersbergen, M., Spreeuw, R.J.C., and Woerdman, J.P.; Orbital Angular Momentum of Light and the Transformation of Laguerre-Gaussian Laser Modes; Physical Review A, vol. 45, No. 11; 8185-8189 (1992).

Anderson, Jorgen Bach; Rappaport, Theodore S.; Yoshida, Susumu; Propagation Measurements and Models for Wireless Communications Channels; 33 42-49 (1995).

Iskander, Magdy F.; Propagation Prediction Models for Wireless Communication Systems; IEEE Transactions on Microwave Theory and Techniques, vol. 50., No. 3, 662-673 (2002).

Wang, Jian, et al.; Terabit free-space data transmission employing orbital angular momentum multiplexing. Nature Photonics; 6, 488-496 (2012).

Katayama, Y., et al.; Wireless Data Center Networking with Steered-Beam mmWave Links; IEEE Wireless Communication Network Conference; 2011, 2179-2184 (2011).

Molina-Terriza, G., et al.; Management of the Angular Momentum of Light: Preparation of Photons in Multidimensional Vector States of Angular Momentum; Physical Review Letters; vol. 88, No. 1; 77, 013601/1-4 (2002).

Rapport, T.S.; Millimeter Wave Mobile Communications for 5G Cellular: It Will Work!; IEEE Access, 1, 335-349 (2013).

PCT: International Preliminary Report on Patentability for PCT/US15/25105 (related application), Oct. 12, 2016, 5 pgs.

Molina, Gabriel et al., Twisted photons. Nature Physics 3, 305-310 (2007). Accessed from the internet <http://www.nature.com/nphys/journal/v3/n5/abs/nphys607.html>. Retrieved <Jun. 12, 2015>.

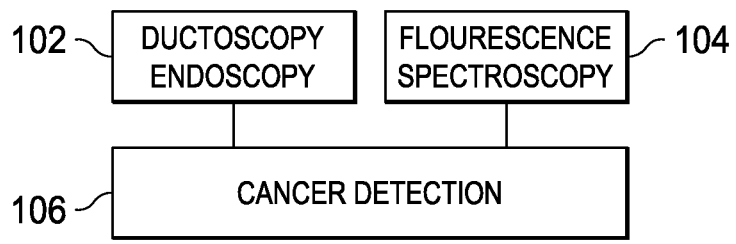
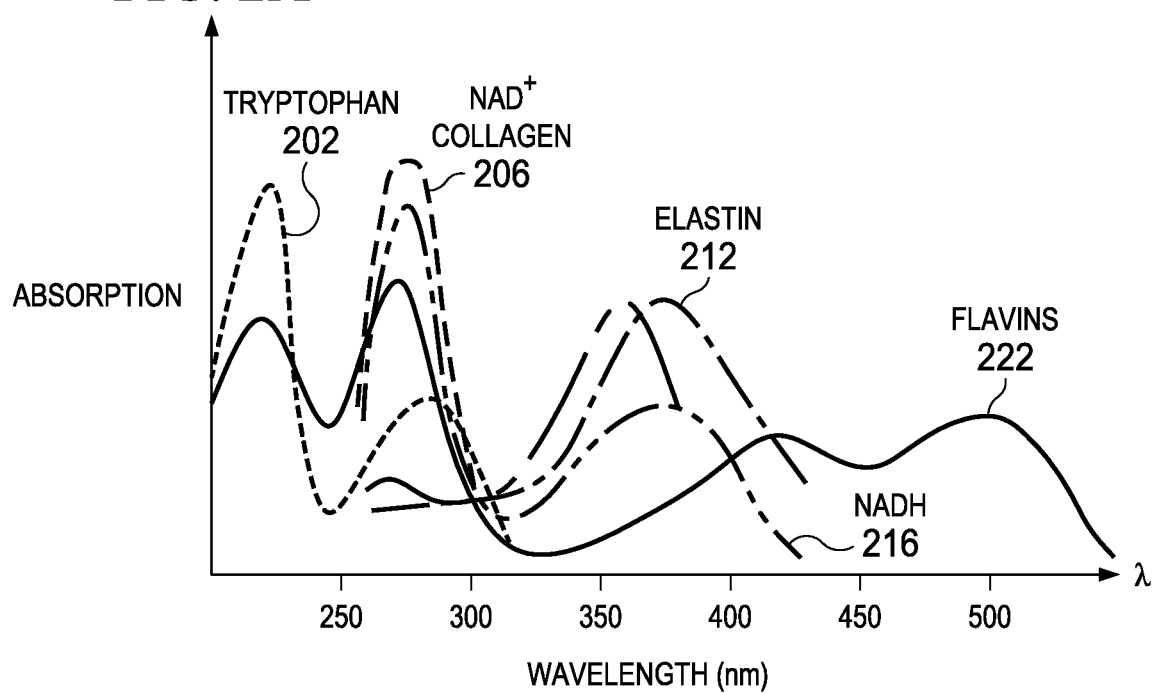

ORBITAL ANGULAR MOMENTUM AND FLUORESCENCE-BASED MICROENDOSCOPE SPECTROSCOPY FOR CANCER DIAGNOSIS

CROSS-REFERENCE TO RELATED APPLICATIONS

This application claims benefit of U.S. Provisional Application No. 61/977,456, filed Apr. 9, 2014, entitled ORBITAL ANGULAR MOMENTUM AND FLUORESCENCE-BASED MICROENDOSCOPE SPECTROSCOPY FOR CANCER DIAGNOSIS, the specification of which is herein incorporated by reference in its entirety.

TECHNICAL FIELD

The present invention relates to microendoscope spectroscopy, and more particularly, to orbital angular momentum and fluorescence-based microendoscope spectroscopy.

BACKGROUND

The spectroscopic identification of malignant tissues, termed "Optical Biopsy", has been investigated for over two decades. Research has shown that native tissue fluorescence can identify malignant and pre-malignant tissues with high accuracy and in real-time. The real-time nature of fluorescence detection makes it an ideal technology for integration into image guided intervention systems, in which fluorescence will identify regions of cancerous and pre-cancerous tissues in real-time. This is normally followed by immediate treatment such as surgery, laser ablation or cauterization. The ability to detect cancerous tissues is of great benefit in a number of patient-care care areas, including breast cancer, skin cancer, ovarian cancer, gynecological cancer and choriocarcinoma. Treatment of digestive cancers such as esophageal, stomach, pancreas, liver, colon, rectal and anal would benefit from this technique. The treatment of urinary cancers such as kidney, bladder, testis and prostate would also benefit. These types of systems also benefit in the treatment of tumors such as carcinoid, nasophayngeal, retroperitoneal sarcomas, and soft tissue.

Among cancers affecting women in the U.S., breast cancer is the second leading cause of death. Standard screening methods such as mammography and ultrasound are ineffectual on younger women with dense breasts, and suffer from high false positive rates. Mammary ductoscopy was developed as a tool to enable physicians to visualize the milk ducts in women at high risk for developing breast cancer. However, ductoscopy also has a significant number of false positive indications when detecting cancer. Thus, there is a need for an improvement in the techniques for detecting cancerous materials when using microendoscopic detection techniques such as that used in mammary ductoscopy.

Most breast cancers start in the epithelial lining of the milk ducts or lobules. These are slow growing cancers which may exist for a long time, while remaining too small (<5 mm) to be detected by mammography, MRI or ultrasound. In an effort to detect small tumors, the ductoscopy technique was developed. In ductoscopy, the internal breast duct anatomy is visualized by endoscopy. In the procedure, the ducts are insufflated and a small diameter micro-endoscope (ductoscope) is inserted into the ducts. This procedure allows visual examination of the ducts as well as the ability to aspirate cells for cytology. However, the number of cells aspirated is small, and the effect of sampling errors on the accuracy of ductoscopy has not been evaluated. Ductoscope working channels are too narrow to allow biopsy samples to be taken during an examination. Ductoscopy is currently being used on patients with a high risk of developing breast cancer. The criteria include patients having each of the following, nipple discharge, having known breast cancer undergoing lumpectomy and patients having a high risk for developing cancer but having normal breast exams.

Various detection methods for certain types of cancer, such as breast cancer, involve the use of techniques such as ductoscopy. Ductoscopy, also referred to as mammary endoscopy, involves the insertion of a small fiber optic scope into the ductal openings of the nipple to look at the lining of the ductal system on a monitor or screen. This provides a window into the ductal system to help identify abnormalities. Often times, cells can be collected after the duct has been visualized with ductal lavage. The development of newer and more usable ductoscopes has enabled ductoscopy to be more easily performed in the operating room or the outpatient setting.

Ductoscopy is presently performed either during surgery or in an outpatient setting. Ductoscopy is often performed in the operating room as part of the surgical procedure to identify, remove and treat the cause of discharge from the breast. Typically, a numbing cream is applied to the nipple anywhere from thirty minutes to two hours prior to the procedure. The nipple is cleaned and made numb with a local anesthetic. By inserting the scope into the ductal orifice having the discharge, the clinician is able to see the abnormality causing the discharge and identify the best place to make a surgical incision to remove any papilloma. Ductoscopy may also be performed within an outpatient setting as it takes a relatively short period of time to perform and causes minimal discomfort.

Another manner for examining for potentially cancerous tissues is the use of ductal lavage to identify cancerous and precancerous cells in the milk ducts of the breast. The procedure can be done in a doctor's office and involves inserting a small catheter into the ductal opening of the nipple and washing out cells from inside the duct. The cells are analyzed by a pathologist who is trained to assess whether they are normal or have begun to look abnormal in ways that indicate they may be moving toward becoming cancerous.

Mammary ductoscopy was initially performed with pediatric endoscopes. Early ductoscopes had several drawbacks which limited their effectiveness. These limitations included the inability to insufflate ducts, the inability to cannulate smaller ductal openings, a lack of a channel to aspirate cells and poor image quality. Newer generations of micro-endoscopes are now available and FDA approved. Two approved commercial micro endoscopes are the VIaDuct® mammary ductoscopes from Acueity and the Mastascope® from Lifeline Biotechnologies. However, these units suffer from a number of limitations. Thus, there is a need for an improved manner of ductoscopy/endoscopy for tissue examination.

SUMMARY

A second method illustrated in FIG. 20 will use time-gating control 2002 to temporarily separate fluorescence measurements detection 2004 from the video lamp 2006. In this scheme, the time gating control 2002 pulls both the video and fluorescence light sources and the photo detection circuitry 2006 is gated. Fluorescence data can only be collected while the UV excitation source is on and the video lamp is off. Since the video is interlaced, the ultraviolet source can be pulsed at 60 Hz to give 60 fields per second (30 frames per second). The fluorescence excitation can be fired at twice the repetition rate of the video system to give increased fluorescence signals. Since the fluorescence lifetime is typically nanoseconds, and the light source pulse width is less than 10 μs for a xenon lamp or less than 10 nanoseconds for an LED. It is possible to pulse the fluorescence source at a frequency many times greater than the video system.

BRIEF DESCRIPTION OF THE DRAWINGS

For a more complete understanding, reference is now made to the following description taken in conjunction with the accompanying Drawings in which:

FIG. 1 is a block diagram illustrating the manner in which a combination of ductoscopy or endoscopy with fluorescence spectroscopy to improve cancer detection;

FIG. 2A illustrates the absorption spectra of key native tissue fluorospheres;

DETAILED DESCRIPTION

Figure 2B:
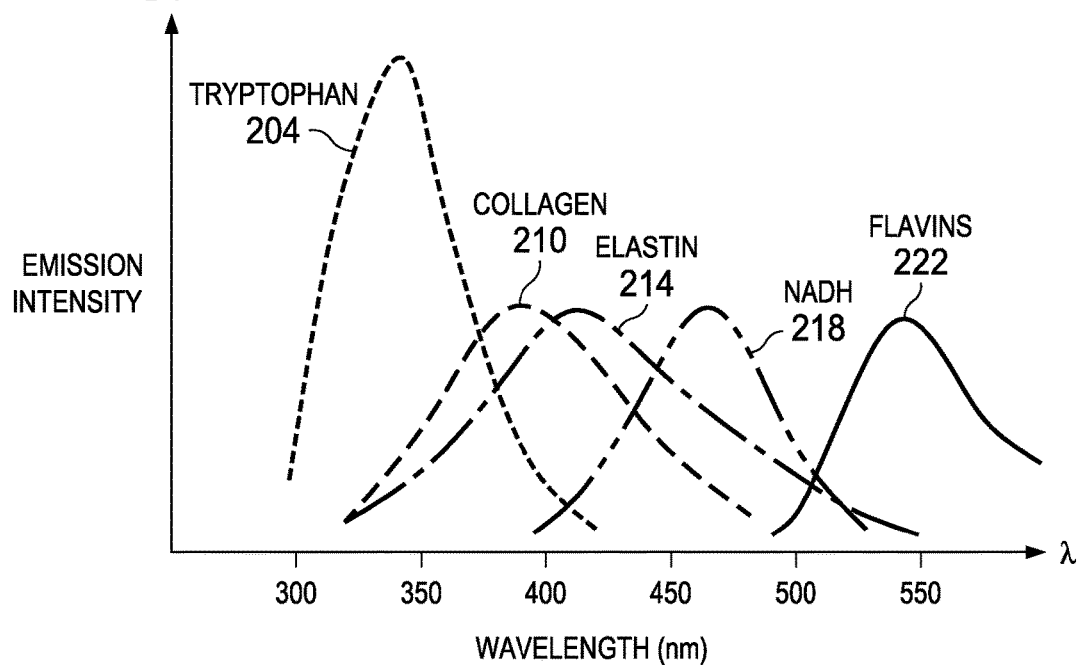
FIG. 2B illustrates the emissions spectra of key native tissue fluorospheres.

Referring now to the drawings, wherein like reference numbers are used herein to designate like elements throughout, the various views and embodiments of orbital angular momentum and fluorescence-based microendoscope spectroscopy for cancer diagnosis are illustrated and described, and other possible embodiments are described. The figures are not necessarily drawn to scale, and in some instances the drawings have been exaggerated and/or simplified in places for illustrative purposes only. One of ordinary skill in the art will appreciate the many possible applications and variations based on the following examples of possible embodiments.

One example of an area of implementation of the below described technique is for use in Ductoscopy. Ductoscopy has primarily been investigated on patients with pathologic nipple discharge (PND). This population is well suited for ductoscopy as they frequently demonstrate single-duct discharge, making identification of the ductal orifice easier. Additionally, many of these patients have ductal dilation or ectasia which makes it easier to maneuver the scope. For many patients, ductoscopy is the only method to identify the duct which is the source of the discharge. The majority of women with PND do not have breast cancer. Over 70% of these patients will have an intraductal papilloma which can be localized and excised with the mammary ductoscope in place. PND is generally indicative of breast cancer if the discharge is limited to a single duct and is bloody. The methods used to exam the discharge for malignancy are ductography, cytology and presence of carcinoembryonic antigen, all of which show high false negatives as well as false positives.

The current techniques for Ductoscopy have a very limited diagnostic capability, thus requiring interpretation of images of limited quality and resolution. Images are sometimes partially obscured by fluids in the ducts. Although ductoscopes have a biopsy channel, specimen sizes are in the range of 0.05 mm to 0.2 mm which are too small for cytologists to be absolutely definitive in a diagnosis. To date, ductoscopy studies have not shown that ductoscopy adds any clinical value to patient care or to planned interventions of care. Studies have shown that ductoscopy produces significant rates of false positives which may lead to increased unnecessary breast biopsies and treatment. Also, significant false negatives can lead to cancers not being detected early thus increasing treatment complications at a later date. The reason for this is that the ductoscopy does not provide any standardization of risk assessment of cancer.

One embodiment of the innovation is for use with ductoscopy or endoscopy techniques. Referring now to FIG. 1, a technique for enhancing the ability of ductoscopy or endoscopy 102 to enhance the identification of a typical ductal epithelium is achieved by combining it with the use of fluorescence spectroscopy 104. By combining ductoscopy/endoscopy techniques 102 with fluorescence spectroscopy 104, the detection of cancer cells 106 may be greatly enhanced. The use of fluorescence spectroscopy 104 with ductoscopy/endoscopy 102 can help to target tissue sampling during ductoscopy/endoscopy to increase yield and reduce sampling errors. The integration of fluorescence spectroscopy 104 into ductoscopy/endoscopy 102 will provide additional salient information which will enhance its accuracy. The real-time nature of fluorescence spectroscopy 104 has the potential to provide a platform for combining cancer diagnostics with immediate intervention.

The benefits from fluorescence spectroscopy 104 arise from the fact that there are several native fluorospheres in tissues which fluoresce in the ultraviolet and visible light spectral regions. These fluorescent molecules include tryptophan (trp), collagen, elastin, reduced nicotinamide adenine dinucleotide (NADH) and flavins. Each of the fluorescent molecules has unique absorption and emission spectra as more fully illustrated in FIGS. 2A and 2B, respectively.

FIG. 2A illustrates the absorption spectra of various fluorescent molecules while FIG. 2B illustrates their emission spectra. Line 202 illustrates the absorption spectra of tryptophan and line 204 illustrates the emission spectra of tryptophan. Line 206 illustrates the absorption spectra of collagen and line 210 illustrates the emissions spectra of collagen. Lines 212 and 214 illustrate the absorption and emission spectra of elastin. Line 216 illustrates the absorption spectra of NADH and line 218 illustrates the emission spectra of NADH. Finally, line 220 illustrates the absorption spectra of flavins while line 222 illustrates the emissions spectra of the flavins.

Multiple ex-vivo and in-vivo fluorescence studies have been performed at different institutes. These studies have included tissues from different organ sites, and have demonstrated a high accuracy of cancer detection by fluorescence techniques with respect to investigations of breast, oral cavity, esophagus, lung, gynecological tract and colon based cancers.

Initial investigations of fluorescence spectroscopy have focused on the visible spectral region, primarily with respect to the emission for flavins and porphyrins. Many of these studies have reported high sensitivity but poor specificity. This may have been a result of higher prophyrin concentration resulting from increased bacteria levels within infected tissues. The use of ultraviolet (UV) excitation wavelengths expanded the number of fluorophores that can be excited to include the structural proteins (collagen and elastin), NADH and tryptophan which resulted in increased specificity and sensitivity. One of the proposed embodiments of a microendoscope will include UV transmitting optical fibers which will provide the increase sensitivity and specificity which results from the use of UV excitation wavelengths. Other types of light emitting fibers may also be used to provide desired detection characteristics.

Figure 3:
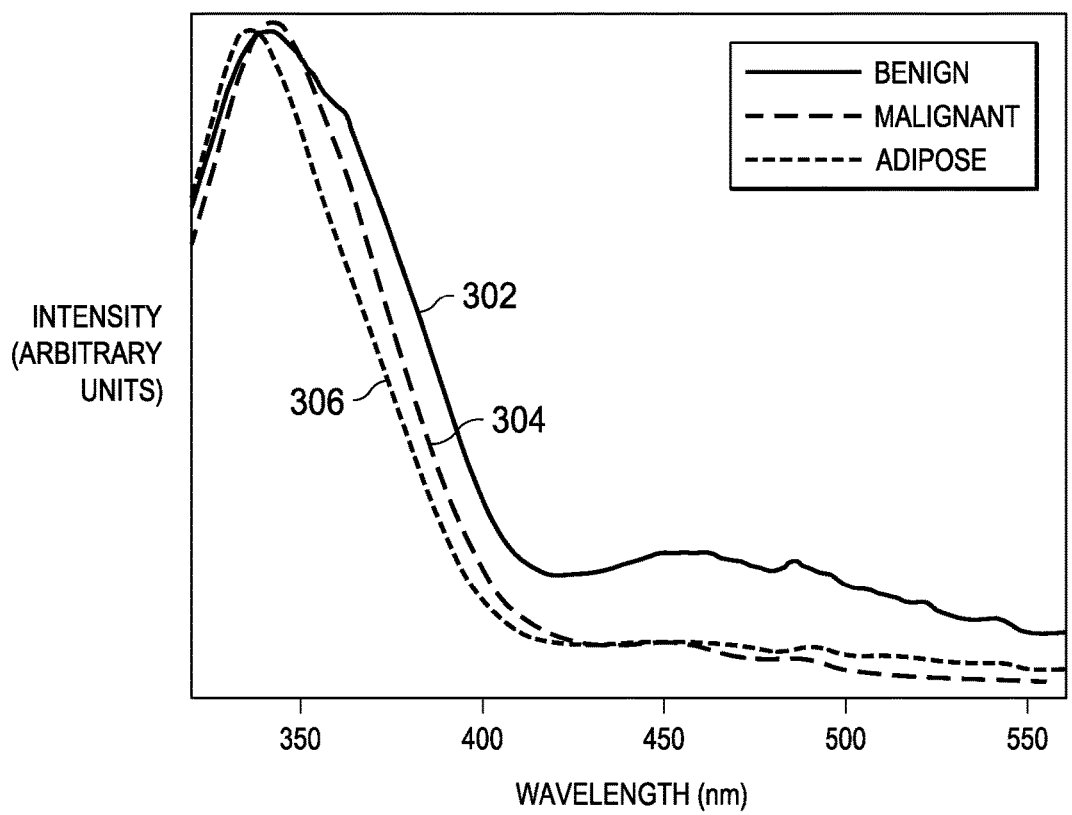
FIG. 3 illustrates the emissions spectra from benign, malignant and adipose ex-vivo human breast tissues excited at 300 nanometers.

The fluorescence properties of human breast tissue have been investigated extensively by some researchers. Emissions, excitation and diffusive reflection spectral measurements were performed on human breast specimens, and the fluorescence signature which can distinguish between malignant tissue, normal tissue and benign tissue were defined. FIG. 3 illustrates the averaged emission spectra for benign tissue 302, the emission spectra for malignant tissue 304 and the emission spectra for adipose tissue 306 ($\lambda_{ex}$=300 nm). The benign tissue spectrum 302 is shifted toward the longer wavelengths and exhibits greater emission intensity in the 400-550 nm range. Using an algorithm based on the ratio of 340 nm to 440 nm emission intensities, the malignant specimens 304 show a higher ratio than the benign specimen 302. The $I_{340}/I_{440}$ ratio was consistently high for malignant breast tissues and low for benign tissues.

Thus, the integration of native fluorescence into microendoscopes can greatly enhance the effectiveness of mammary ductoscopy. However, current microendoscopes are inadequate to use fluorescence. The range of useable transmission wavelengths for commercial microendoscopes ranges from 450 nm to 900 nm. These ranges make commercial microendoscope unsuitable for exciting the tissue fluorophores ($\lambda_{ex}$=250 to 400 nm) which have the greatest diagnostic potential with respect to cancerous tissue. Fluorescence optical biopsy in the visible spectral range can detect changes from cancer with a reduced accuracy of between 60 and 70 percent compared to ultraviolet light excitation.

The advantage of this approach is clear over existing mammary ductoscope techniques because fluorescence ductoscopy may characterize cancerous parts from normal ducts. The microendoscope will be inserted into breast duct openings at the nipple and guided by the physician through the ducts. The physician visually examines the duct for abnormalities and, in addition, will obtain spectroscopic information of suspicious mammary duct areas. The spectra from healthy mammary ducts may be compared to samples taken with the microendoscope and an algorithm can be utilized to compare in real-time the spectra of healthy ducts with spectra taken during an intervention procedure in order to identify cancerous and pre-cancerous lesions.

The fluorescence spectroscopy technique will be utilized through a narrow gauge needle. Fluorescence spectroscopy through a narrow gauge needle introduces several measurement problems. These problems include weaker signals, inefficient excitation light coupling into the fibers, increased stray light leakage and reduced emission due to collection from a smaller area.

Figure 4:
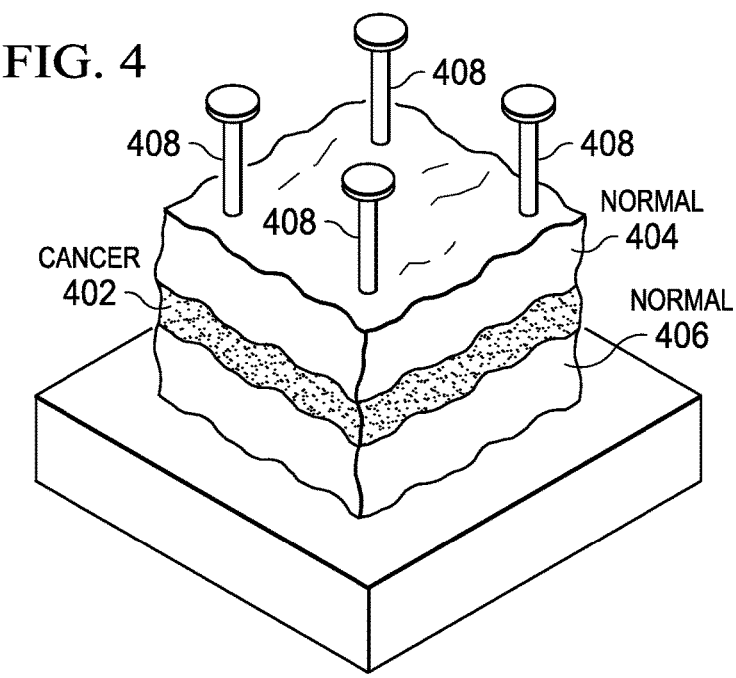
FIG. 4 illustrates a model breast tissues structure consisting of malignant tissue sandwiched between normal tissues.
Figure 5:
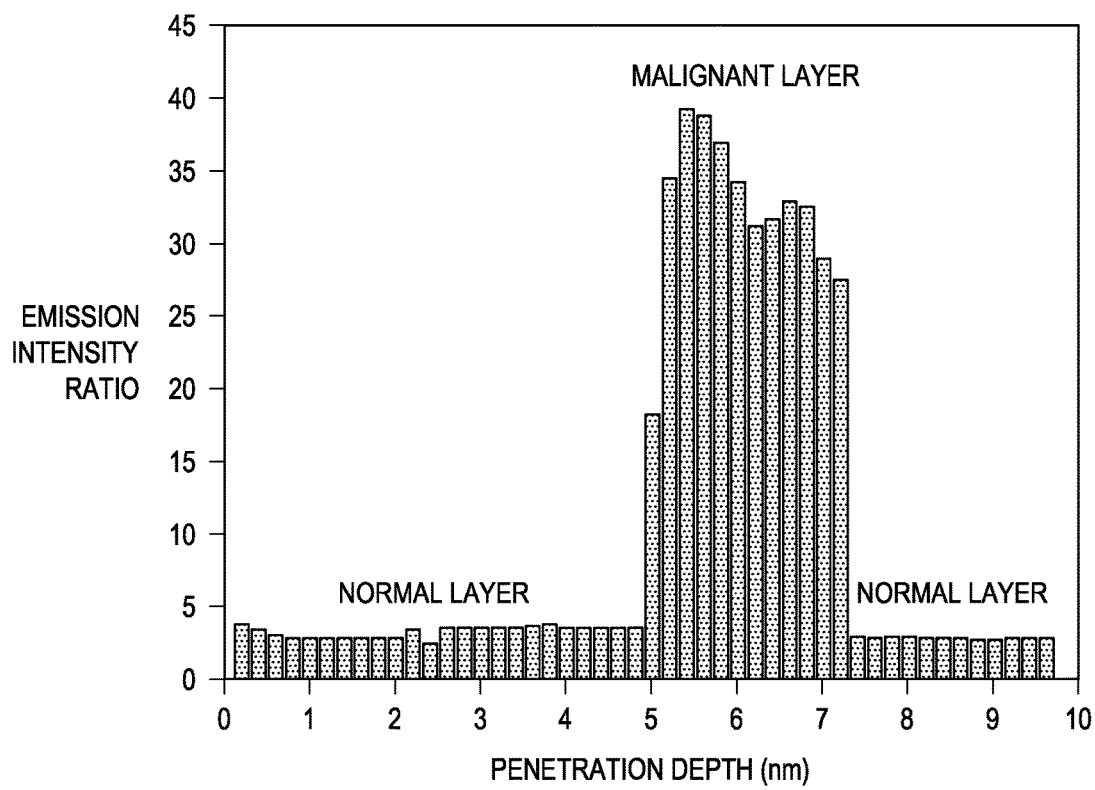
FIG. 5 illustrates the fluoroscope ratio as a function of depth within a tissue sample.

In previous investigations, researchers have investigated the integration of fluorescence spectroscopy into stereotactic needles for use in fine needle aspiration procedures. The structure illustrated in FIG. 4 simulates a malignant tumor 402 surrounded by normal tissue layers 404 and 406. As the needle probes 408 penetrates through the normal tissue and into the tumor tissue, the fluorescence properties change. The $I_{340}/I_{440}$ emission intensity ratio ($\lambda_{ex}$=300 nm) as a function of depth is plotted in FIG. 5. The difference in the emission intensity ratios between the normal layers 404, 406 and the malignant layer is easily seen. From the depth penetration of 0 mm to approximately 5 mm the needle is within a normal layer of tissue and the emission intensity ratio is below 5 nm. As the needle passes through the depth of 5 nm to 7 nm, the emission intensity ratio drastically increases. This represents the malignant layer 402 of FIG. 4. Finally, when the needle leaves the malignant layer 402 and passes back into the normal layer 406, the emission intensity ratio again falls below 5 nm. Thus, there is a definite relationship between the fluorescence ratio as a function of the depth in the sample based upon whether the needle is passing through a normal layer of tissue 404, 406 or a malignant layer of tissue 402.

Figure 6:
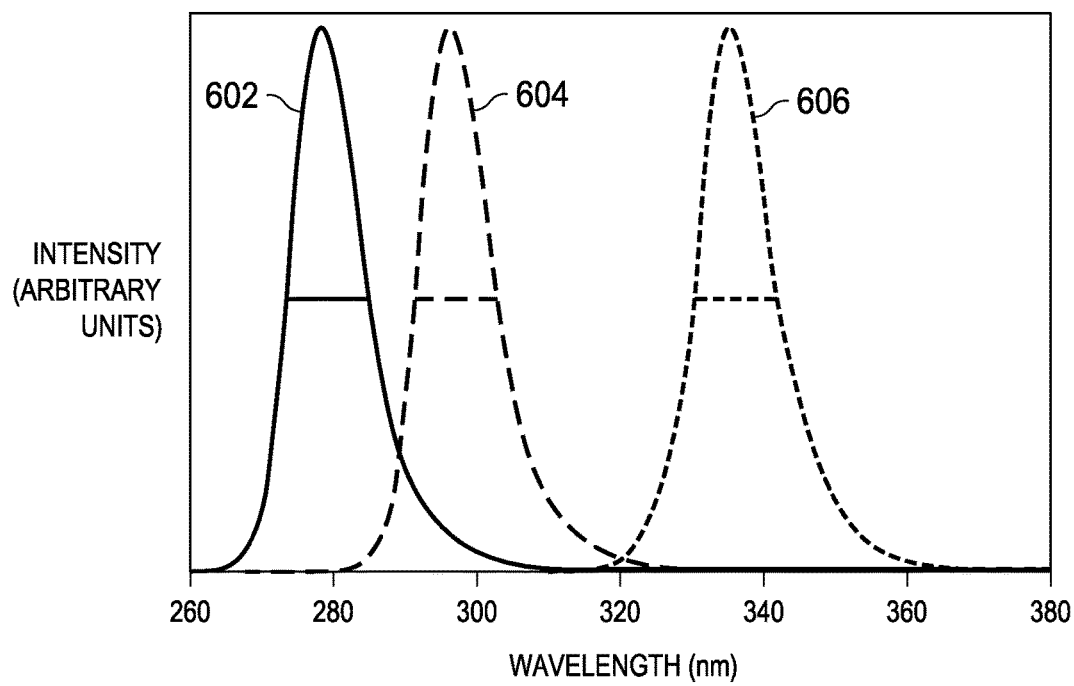
FIG. 6 illustrates the emissions from three ultraviolet LEDs at various wave lengths.
Figure 7:
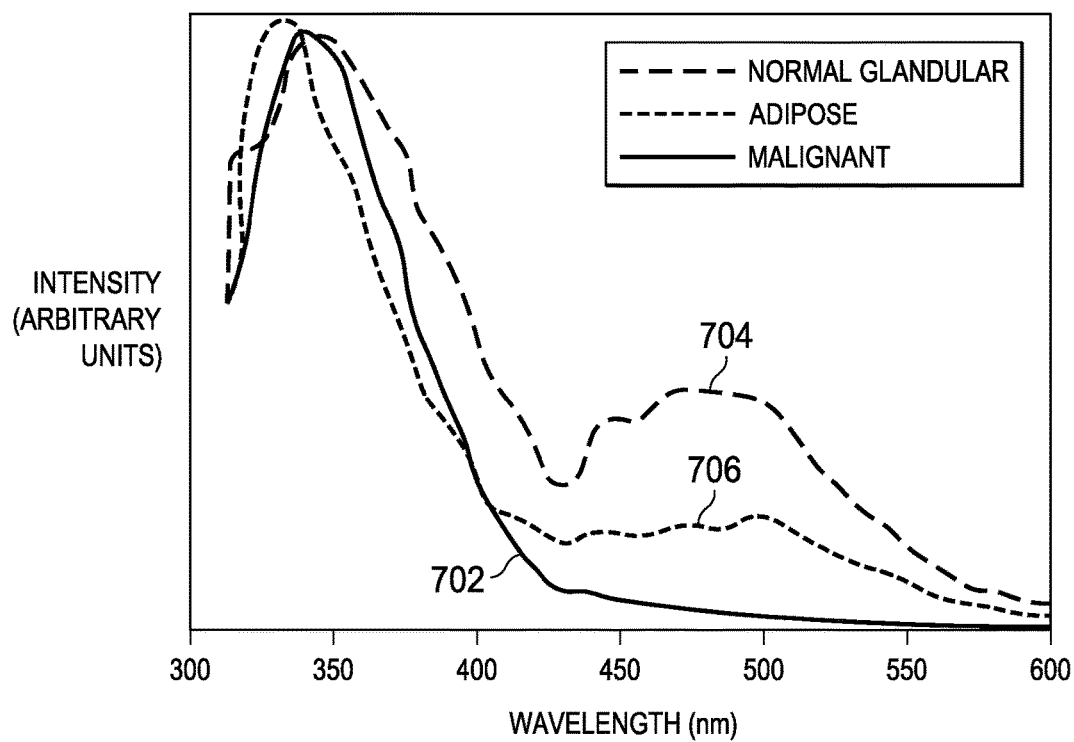
FIG. 7 illustrates the fluorescence from normal, glandular adipose and malignant tissues excited with ultraviolet light.

LEDs based on AlGaN alloys are one potentially new UV source for exciting tissue fluorescence. However, it should be realized that other possible embodiments of LEDs may be used as different types of UV or other types of light sources for tissue fluorescence for cancer detection. LEDs are compact devices that are readily coupled in optical fibers. Since their output is concentrated in a narrow spectral band, LEDs will require less current than xenon lamps and will generate much less out-of-band light leakage. Although not tunable, multiple LEDs can be integrated into a device and provide several excitation wavelengths. The emission profile for three different LEDs is illustrated in FIG. 6. Line 602 illustrates the emission profile at 280 nm. Line 604 represents the emission profile at 300 nm and line 606 illustrates the emission profile at 340 nm. The fluorescence from normal glandular, adipose and malignant breast tissues are illustrated in FIG. 7. As can be seen, the malignant tissue 702 has a much lower intensity between 450 and 600 nm than that of the normal glandular 704 or adipose tissue. However, any source can be used that has characteristics similar to those discussed above.

Figure 8:
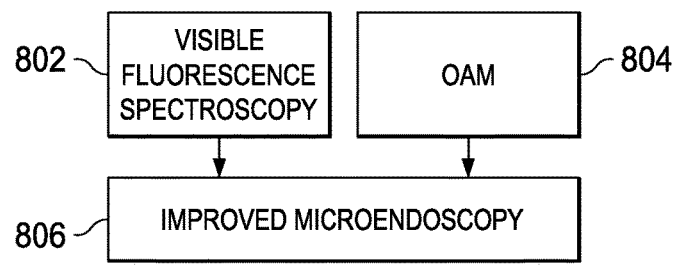
FIG. 8 illustrates the manner in which visible fluorescent spectroscopy may be combined with orbital angular momentum in order to provide improved microendoscopy.

Referring now to FIG. 8, in another embodiment, the improved detection capabilities of visible fluorescence spectroscopy 802 may be further improved by combining therewith the generation of orbital angular momentum within the light streams transmitted through various tissue samples. By combining visible fluorescence spectroscopy 802 with orbital angular momentum techniques 804 an improved microendoscopy may be provided. The orbital angular momentum of light emitted from malignant tissues will have a different OAM from light from tissues that are benign. Algorithmic comparisons of OAM light from normal OAM tissue samples with OAM light from samples taken by the improved microendoscope 806 including an OAM channel within the fluorescent channel will improve the operation of the ductoscopy/microendoscope. By integrating ultraviolet fluorescence spectroscopy 802 with orbital angular momentum processing 804 within microendoscopy, a means for providing real time diagnostic information for cancer detection and identification may be provided. This provides a detection system that has greater reliability and is faster than existing systems. For example, the inclusion of a fluorescence/OAM detection system will increase the ability of ductoscopy to detect small lesions within the breast duct. The fact that this information is available in real time will allow physicians to immediately treat the patient rather than waiting for later analysis. While the foregoing discussion is made with respect to visible fluorescence spectroscopy, other fluorescence techniques may also be used in a similar manner. Additionally other techniques than orbital angular momentum techniques may be used. Any orthogonal function to the light may be used to provide similar detection capabilities.

Figure 9:
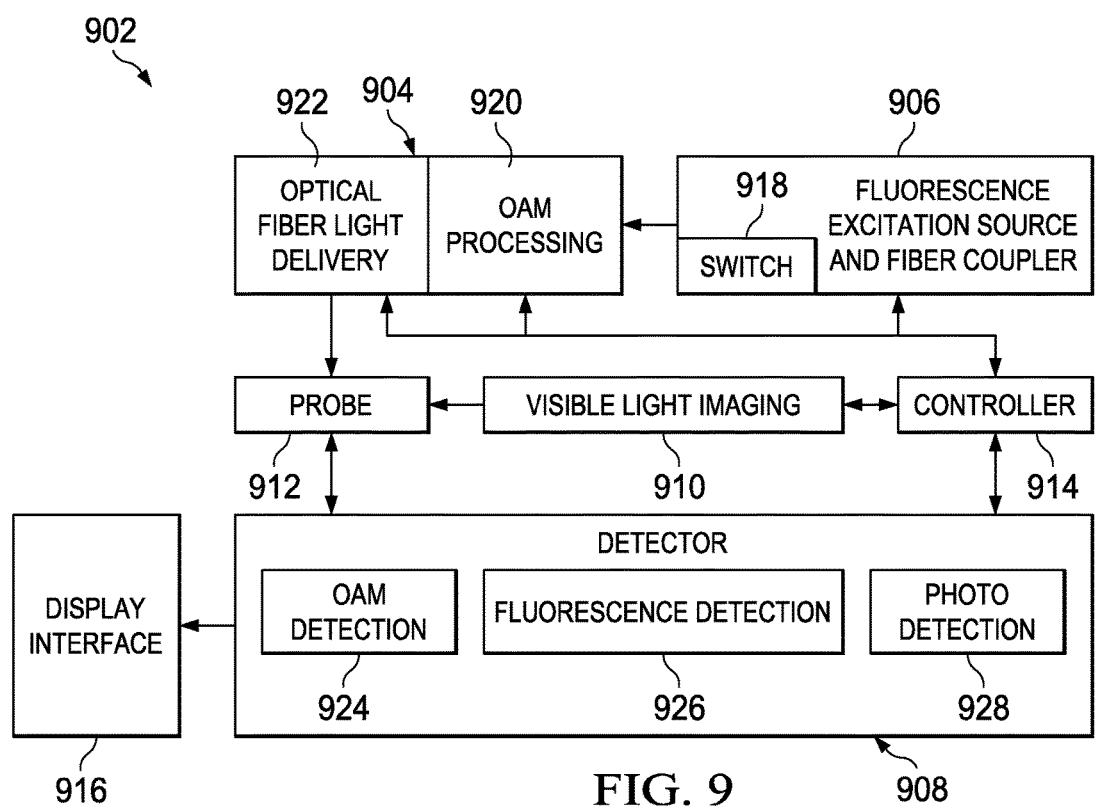
FIG. 9 illustrates a functional block diagram of a system for utilizing fluorescence spectroscopy and orbital angular momentum for the detection of cancerous tissues.
Figure 10:
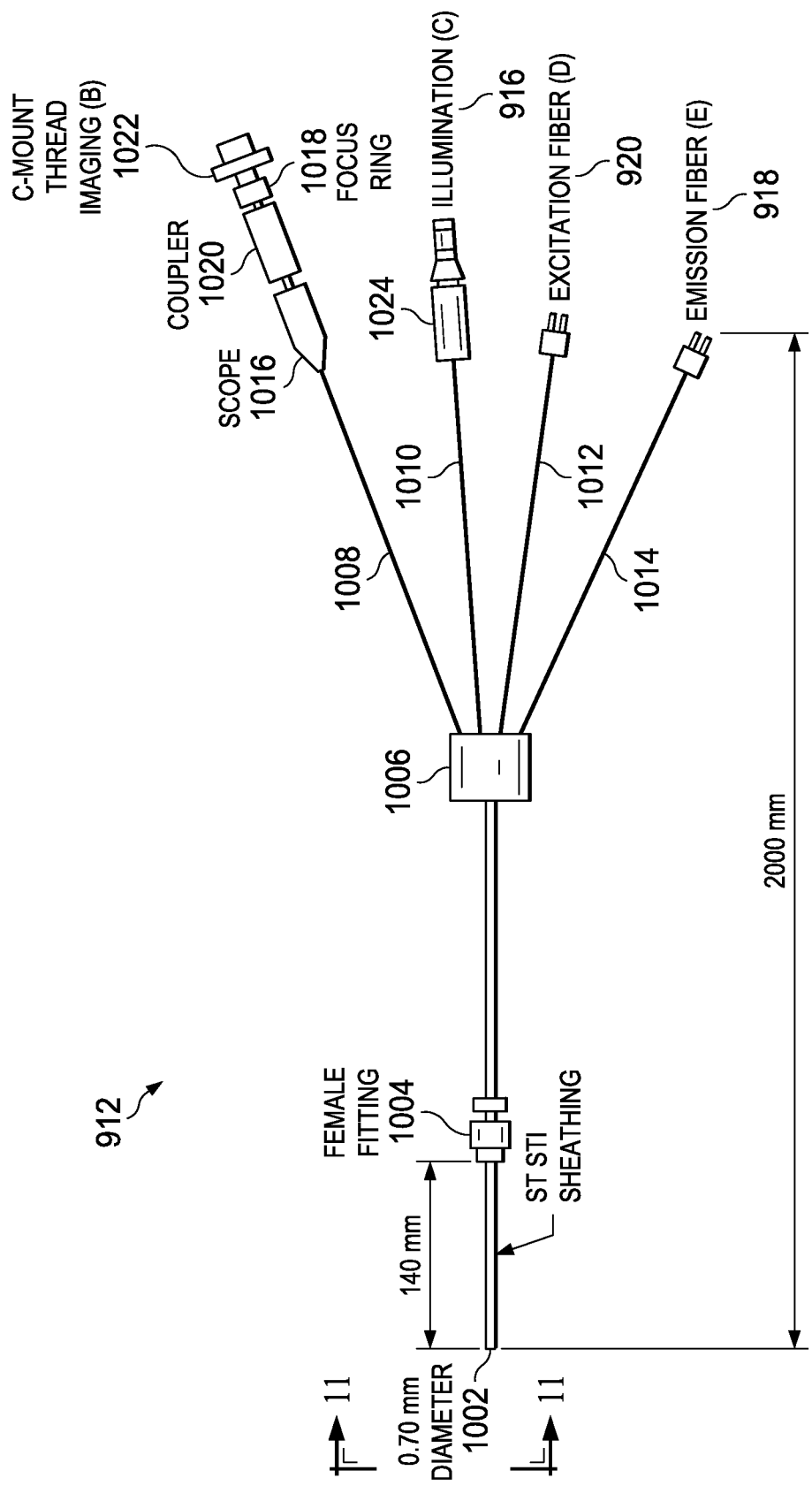
FIG. 10 illustrates a probe for use with the system of FIG. 9.

Referring now to FIG. 9, there is more particularly illustrated one embodiment of a fluorescence/OAM based endoscope 902. However, other embodiments are possible. The fluorescence/OAM endoscope 902 includes a number of subsystems including a UV optical fiber light subsystem with OAM 904, a fluorescence excitation source and fiber coupler 906, a fluorescent/OAM detection subsystem 908, a visible light imaging subsystem 910 and a probe 912. These various subsystems are controlled by a controller 914 and detected information from the detector is displayed via a display interface 916. Fluorescent excitation source and fiber coupler 906 generate a fluorescent light and couples the fiber to the probe 912. The visible light imaging subsystem 910 generates the visible light used with the imaging systems that are provided to the probe 912. The optical fiber light delivery subsystem 904 provides ultraviolet orbital angular momentum twisted light to a probe 804. The fluorescent/OAM detection subsystem 908 is used for detecting fluorescent OAM twisted light within the probe 912 in order to detect potentially cancerous cells. The probe 912 as more fully illustrated in FIG. 10 is inserted into a patient in order to generate the imaging and OAM detection information. The probe 912 consists of an input end 1002 that is inserted into the patient's body in any of a number of openings. The probe input end 1002 in one embodiment is 140 mm long between the tip 1003 and a female fitting 1004. The female fitting 1004 allows various probe input end 1002 of differing sizes and lengths to be connected to the probe 912. The probe input end 1002 includes ST STI sheathing around the probe input end 1002. The sheathing surrounds various fibers that are inserted into the patient's body via the probe input end 1002. The various fibers are interconnected together to be provided out the probe input end 1002 at a junction box 1006.

Interconnecting to the junction box 1006 are a number of different fibers. These include the imaging fiber 1008, the illumination fiber 1010, the excitation fiber 1012 and the emission fiber 1014. The imaging fiber 1008 enables various images (pictures/videos) to be received through the probe input end 1002. The imaging fiber 1008 enables a viewing of picture images coming through the fiber provided to the probe input end 1002. The pictures are taken via a scope 1016 connected with an imaging fiber 1008. The scope 1016 is coupled to a focus ring 1018 via a coupler 1020. The focus ring 1018 enables focusing of the image that is being viewed through the scope 1016. The coupler 1020 provides a means for coupling the focus ring 1018 to the scope 1016. The focus ring 1018 has on its opposite end a C-mount thread 1022 enabling the imaging fiber to be connected various photo detection circuitry as will be more fully described herein below.

Illumination for the images that are taken through the image fiber 1008 is accomplished through the illumination fiber 1010. The illumination fiber 1010 is connected at a coupler 1024 to some type of illumination source. The illumination fibers 1010 may comprise one or more fibers that provide a white light for illumination of the probe area in order to capture images of the area using the imaging fiber 1008. The excitation fiber 1012 is used for projecting an ultraviolet light having an orbital angular momentum twist applied thereto that is output from the probe tip 1003 to a probe area. Responses to this ultraviolet twisted light from illuminated tissues may be detected through the emission fiber 1014 that allows the monitoring of OAM twisted UV signals radiating from various cells within the body that are being illuminated by the probe 912.

Figure 11:
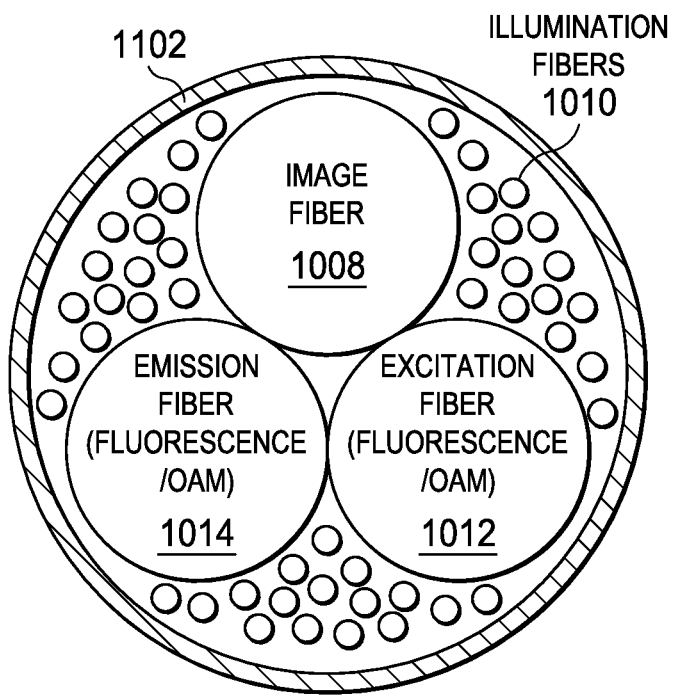
FIG. 11 is a cross-sectional view of the fiber utilized within the probe of FIG. 10.

Referring now also to FIG. 11, there is illustrated a cross sectional view of the probe input end 1002. The body of the probe input end 1002 is surrounded by an external sheathing 1102. Within the external sheathing 1102 are included the plurality of illumination fibers 1010 that provide the white light illumination for the imaging fiber 1008. Visual images are captured by the imaging fiber 1008 using the provided white light from the illumination fibers 1010. The excitation fiber 1012 provides the ultraviolet OAM twisted light signals to the patient's body and responses to the OAM twisted UV light are detected through the emissions fiber 1014.

Referring now back to FIG. 9, the fluorescence excitation source 906 may comprise a number of differing components. Traditional light sources for broad band illumination in the ultraviolet range have been provided from xenon arc lamp. Alternative configurations may use ultraviolet emitting LEDs based on AlGaN alloy devices. LEDs at 280 nm, 300 nm and 340 nm can be used in this configuration. Ultraviolet LEDs concentrate their emissions into a narrow spectral bandwidth and therefore may be able to provide more usable power than a brighter xenon lamp. The narrower emission of an LED will also result in less out-of-band light leakage through the excitation fiber 1012. The geometry of an LED will allow more efficient coupling into smaller diameter fibers than a xenon arc lamp. LEDs are significantly smaller than xenon lamps and draw less current. However, multiple LEDs emitting at different wavelengths will be needed in order to excite several different tissue fluorophores which will require a fiber switch 918 to be incorporated into the excitation source 906 to select a desired wavelength. Other types of light may also be utilized as may other types of orthogonal functions in addition to an OAM processed light signal.

The excitation power provided from the fluorescence excitation source 906 should achieve an excitation power at the sample site of at least 10 µW at each excitation wavelength and reduce the out-of-band light leakage to a factor of $10^{-4}$ less than the excitation power. Fluorescence spectra will be acquired with the excitation source 906 and the signal-to-noise level determined for each source. The signal-to-noise ratio from the two excitation light sources will be compared for both scattering samples and non-scattering samples. The light source with better SNR will be selected for microendoscopy. The UV source from the fluorescent excitation source 906 is provided to the optical fiber light delivery and OAM processing circuitry 920. The OAM processing circuitry 920 can provide different orbital angular momentum twists to the ultraviolet signal from the excitation source 906. As described previously other orthogonal function processing techniques may also be utilized rather than OAM processing. The particular orbital angular momentum twist may be selected based upon the particular type of cancerous material being monitored for. Different tissues will respond with OAM fluorescence signatures that are unique to the type of cancer being detected. The UV/OAM twisted light will be selected to provide a desired signature response.

Using the orbital angular momentum state of the transmitted energy signals, physical information can be embedded within the electromagnetic radiation transmitted by the signals. The Maxwell-Heaviside equations can be represented as:

$$\nabla \cdot E = \frac{\rho}{\varepsilon_0}$$

$$\nabla \times E = -\frac{\partial B}{\partial t}$$

$$\nabla \cdot B = 0$$

$$\nabla \times B = \varepsilon_0 \mu_0 \frac{\partial E}{\partial t} + \mu_0 j(t, x) \text{the}$$

where $\nabla$ is the del operator, E is the electric field intensity and B is the magnetic flux density. Using these equations, we can derive 23 symmetries/conserve quantities from Maxwell's original equations. However, there are only ten well-known conserve quantities and only a few of these are commercially used. Historically if Maxwell's equations where kept in their original quaternion forms, it would have been easier to see the symmetries/conserved quantities, but when they were modified to their present vectorial form by Heaviside, it became more difficult to see such inherent symmetries in Maxwell's equations.

The conserved quantities and the electromagnetic field can be represented according to the conservation of system energy and the conservation of system linear momentum. Time symmetry, i.e. the conservation of system energy can be represented using Poynting's theorem according to the equations:

$$H = \sum_i m_i \gamma_i c^2 + \frac{\varepsilon_0}{2} \int d^3 x (|E|^2 + c^2 |B|^2)$$

-continued $$\frac{dU^{mech}}{dt} + \frac{dU^{em}}{dt} + \oint_{s'} d^2 x' \hat{n}' \cdot S = 0$$

The space symmetry, i.e., the conservation of system linear momentum representing the electromagnetic Doppler shift can be represented by the equations:

$$P = \sum_i m_i \gamma_i v_i + \varepsilon_0 \int d^3 x (E \times B)$$

$$\frac{dp^{mech}}{dt} + \frac{dp^{em}}{dt} + \oint_{s'} d^2 x' \hat{n}' \cdot T = 0$$

The conservation of system center of energy is represented by the equation:

$$R = \frac{1}{H} \sum_i (x_i - x_0) m_i \gamma_i c^2 + \frac{\varepsilon_0}{2H} \int d^3 x (x - x_0)(|E|^2 + c^2 |B|^2)$$

Similarly, the conservation of system angular momentum, which gives rise to the azimuthal Doppler shift is represented by the equation:

$$\frac{dJ^{mech}}{dt} + \frac{dJ^{em}}{dt} + \oint_{s'} d^2 x' \hat{n}' \cdot M = 0$$

For radiation beams in free space, the EM field angular momentum $J^{em}$ can be separated into two parts:

$$J^{em} = \varepsilon_0 \int_{V'} d^3 x' (E \times A) + \varepsilon_0 \int_{V'} d^3 x' E_i [(x' - x_0) \times \nabla] A_i$$

For each singular Fourier mode in real valued representation:

$$J^{em} = -i \frac{\varepsilon_0}{2\omega} \int_{V'} d^3 x' (E^* \times E) - i \frac{\varepsilon_0}{2\omega} \int_{V'} d^3 x' E_i [(x' - x_0) \times \nabla] E_i$$

The first part is the EM spin angular momentum $S^{em}$, its classical manifestation is wave polarization. And the second part is the EM orbital angular momentum $L^{em}$ (or other orthogonal function) its classical manifestation is wave helicity. In general, both EM linear momentum $P^{em}$, and EM angular momentum $J^{em} = L^{em} + S^{em}$ are radiated all the way to the far field.

By using Poynting theorem, the optical vorticity of the signals may be determined according to the optical velocity equation:

$$\frac{\partial U}{\partial t} + \nabla \cdot S = 0,$$

where S is the Poynting vector $$S = \frac{1}{4}(E \times H^* + E^* \times H),$$

and U is the energy density $$U = \frac{1}{4}(\varepsilon|E|^2 + \mu_0|H|^2),$$

with E and H comprising the electric field and the magnetic field, respectively, and $\varepsilon$ and $\mu_0$ being the permittivity and the permeability of the medium, respectively. The optical voracity V may then be determined by the curl of the optical velocity according to the equation:

$$V = \nabla \times v_{opt} = \nabla \times \left( \frac{E \times H^* + E^* \times H}{\varepsilon|E|^2 + \mu_0|H|^2} \right)$$

The creation and detection of one embodiment using orbital angular momentum signals and the fibers of the detection device will now be more fully discussed. However, any orthogonal function can be used, including Jacobi functions, Gegenbauer functions, Legendre functions, Chebyshev functions, Laguerre functions, Gaussian functions, ect.

This orbital angular momentum process signals are provided to the optical fiber light delivery system 922 that transmits the UV OAM twisted light down the excitation fiber 920.

The detector subsystem 908 consists of OAM detection 924, fluorescence detection circuitry 926 and photo detection circuitry 928. The OAM detection circuitry 924 detects OAM twists (or in other embodiments other orthogonal functions) within the ultraviolet light signals detected over the emission fiber 1014 of the probe 912. The OAM detection circuitry 924 can detect the OAM twists within the received ultraviolet signal and compare this with other known OAM signatures of both benign and malignant tissue to perform an analysis with respect to tissue being monitored by the probe 912. In a similar fashion, the fluorescence detection circuitry 926 will compare the fluorescence of various tissues being monitored by the probe 912 to known fluorescence samples to determine if the fluorescence that is detected provides any indication of malignant or benign tissues under study. The known OAM signatures and fluorescence signatures may be stored in an associated database.

The photo detection circuitry 926 may be connected to the C-mounted thread 1022 of the imaging fiber 1008 in order to provide actual images of the tissues that are directly before the probe tip 1002. The images that are provided to the photo detection circuitry 1028 and the detections made by the OAM detection circuitry 924 and fluorescence detection circuitry 926 may be provided to a display interface 916 that displays the information that has been detected in a manner that may be analyzed and interpreted by a surgeon or technician that is utilizing the microendoscope. All of the components within the system 902 are under the control of a controller 914 that provides various control signals relating to the operations thereof. The controller 914 may also control comparisons of OAM and fluorescence signatures that are detected with stored signatures. The controller 914 may use physician-friendly software to control the endoscope measurement parameters, collect and save fluoroscope/OAM data and display both the images and fluorescence data in an easy to interpret format on the display interface 916. Any software can be used to display the data and store it. In one embodiment, LabView™ can be used which allows for rapid design, development and debugging of software. LabView™ drivers are available to control many different types of scientific instruments which facilitates the integration of different components of the endoscope (i.e. video, photo detection, excitation timing).

The visible light imaging subsystem 910 provides the white light to the probe 912 that is output via the illumination fibers 1010. This white light is used for the taking of pictures through the imaging fiber 1028 that are detected by the photo detection circuitry 928.

Figure 12:
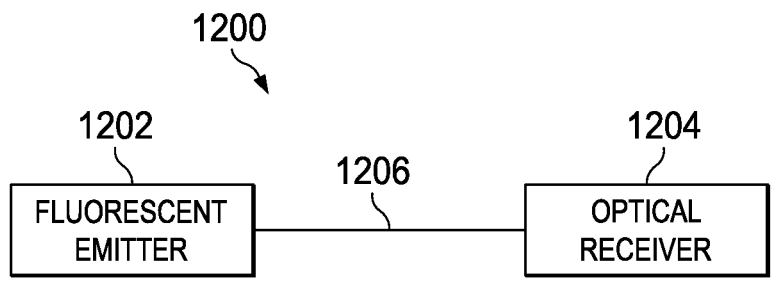
FIG. 12 illustrates the transmission of information on an emission fiber or excitation fiber.

The use of orbital angular momentum (or other orthogonal function) signatures and fluorescence signatures within a microendoscope provides for optical fiber communication of the information over the emission fiber 1206. FIG. 12 illustrates the manner in which fluorescent light emitted from a fluorescent emitter 1202 or the cells being excited via a fluorescent OAM twisted light source are received at an optical receiver 1204 over an emission fiber/emission fiber 1206. The fluorescent emitter 1202 provides information within the light wavelength or wavelengths that is propagated over the optical fiber 1206 to the optical receiver 1204. The fibers 1206 of the probe 912 may comprise a variety of fiber types as discussed below.

Figure 13A:
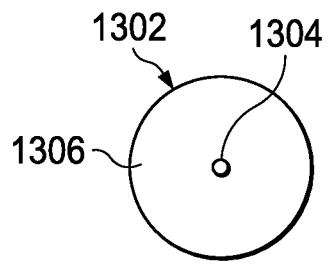
FIG. 13A illustrates a single mode fiber.
Figure 13B:
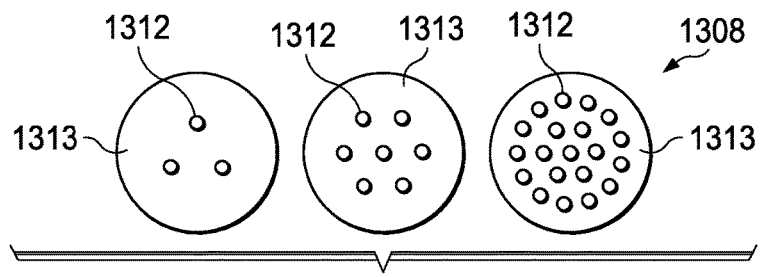
FIG. 13B illustrates multi-core fibers.
Figure 13C:
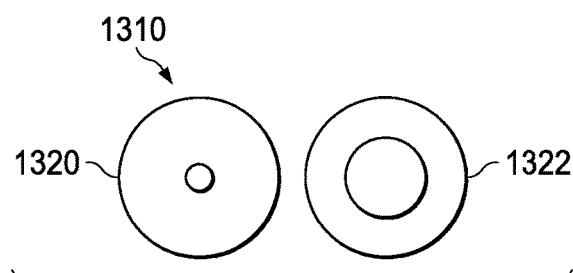
FIG. 13C illustrates multi-mode fibers.
Figure 13D:
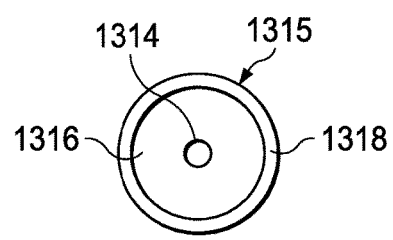
FIG. 13D illustrates a hollow cord fiber.

Referring now to FIGS. 13A-13C, there is more particularly illustrated the single mode fiber 1302, multicore fibers 1308, and multimode fibers 1310 described herein above. The multicore fibers 1308 consist of multiple cores 1312 included within the cladding 1313 of the fiber. As can be seen in FIG. 13B, there are illustrated a 3 core fiber, 7 core fiber, and 19 core fiber. Multimode fibers 1310 comprise multimode fibers comprising a few mode fiber 1320 and a multimode fiber 1322. Finally, there is illustrated a hollow core fiber 1315 including a hollow core 1314 within the center of the cladding 1316 and sheathing 1318.

Single mode fibers (SMFs) 1302 is illustrated in FIG. 13A support propagation of two orthogonal polarizations of the fundamental mode only (N=2). For sufficiently large core radius and/or the core cladding difference, a fiber is multi-moded for N>2 as illustrated in FIG. 13C. For optical signals having orbital angular momentums (or other orthogonal functions) and multilayer modulation schemes applied thereto, multimode fibers 1310 that are weakly guided may be used. Weakly guided fibers have a core cladding refractive index difference that is very small. Most glass fibers manufactured today are weakly guided, with the exception of some photonic crystal fibers and air-core fibers. Fiber guide modes of multimode fibers 1310 may be associated in step indexed groups where, within each group, modes typically having similar effective indexes are grouped together. Within a group, the modes are degenerate. However, these degeneracies can be broken in a certain fiber profile design.

We start by describing translationally invariant waveguide with refractive index n=n(x, y), with $n_{co}$ being maximum refractive index ("core" of a waveguide), and $n_{cl}$ being refractive index of the uniform cladding, and $\rho$ represents the maximum radius of the refractive index n. Due to translational invariance the solutions (or modes) for this waveguide can be written as:

$$E_j(x,y,z) = e_j(x,y)e^{i\beta_j z},$$

$$H_j(x,y,z) = h_j(x,y)e^{i\beta_j z},$$

where $\beta_j$ is the propagation constant of the j-th mode. Vector wave equation for source free Maxwell's equation can be written in this case as:

$$(\nabla^2 + n^2 k^2 - \beta_j^2) e_j = -(\nabla_t + i\beta_j \hat{z})(e_{t,j} \cdot \nabla_t \ln(n^2))$$

$$(\nabla^2 + n^2 k^2 - \beta_j^2) h_j = -(\nabla_t \ln(n^2)) \times ([(\nabla)]_t + i\beta_j \hat{z}) \times h_j)$$

where $k=2\pi/\lambda$ is the free-space wavenumber, $\lambda$ is a free-space wavelength, $e_t=e_x\hat{x}+e_y\hat{y}$ is a transverse part of the electric field, $\nabla^2$ is a transverse Laplacian and $\nabla_t$ transverse vector gradient operator. Waveguide polarization properties are built into the wave equation through the $\nabla_t \ln(n^2)$ terms and ignoring them would lead to the scalar wave equation, with linearly polarized modes. While previous equations satisfy arbitrary waveguide profile n(x, y), in most cases of interest, profile height parameter $\nabla$ can be considered small $\nabla \ll 1$, in which case waveguide is said to be weakly guided, or that weakly guided approximation (WGA) holds. If this is the case, a perturbation theory can be applied to approximate the solutions as:

$$E(x,y,z)=e(x,y)e^{i(\beta+\hat{\beta})z}=(e_t+\hat{z}e_z)e^{i(\beta+\hat{\beta})z}$$

$$H(x,y,z)=h(x,y)e^{i(\beta+\hat{\beta})z}=(h_t+\hat{z}h_z)e^{i(\beta+\hat{\beta})z}$$

where subscripts t and z denote transverse and longitudinal components respectively. Longitudinal components can be considered much smaller in WGA and we can approximate (but not neglect) them as:

$$e_z = \frac{i(2\Delta)^{\frac{1}{2}}}{V}(\rho\nabla_t \cdot e_t)$$

$$h_z = \frac{i(2\Delta)^{\frac{1}{2}}}{V}(\rho\nabla_t \cdot h_t)$$

Where $\Delta$ and V are profile height and fiber parameters and transversal components satisfy the simplified wave equation.

$$(\nabla^2 n^2 k^2 - \beta_j^2)e_j = 0$$

Though WGA simplified the waveguide equation, further simplification can be obtained by assuming circularly symmetric waveguide (such as ideal fiber). If this is the case refractive index that can be written as:

$$n(r)=n^2_{co}(1-2f(R)\Delta)$$

where $f(R) \geq 0$ is a small arbitrary profile variation.

For a circularly symmetric waveguide, we would have propagation constants $\beta_{lm}$ that are classified using azimuthal (l) and radial (m) numbers. Another classification uses effective indices $n_{lm}$ (sometimes noted as $n^{eff}_{lm}$ or simply $n_{eff}$, that are related to propagation constant as: $\beta_{lm}=kn^{eff}$). For the case of l=0, the solutions can be separated into two classes that have either transverse electric ($TE_{0m}$) or transverse magnetic ($TM_{0m}$) fields (called meridional modes). In the case of l≠0, both electric and magnetic field have z-component, and depending on which one is more dominant, so-called hybrid modes are denoted as: $HE_{lm}$ and $EH_{lm}$.

Polarization correction $\delta\beta$ has different values within the same group of modes with the same orbital number (l), even in the circularly symmetric fiber. This is an important observation that led to development of a special type of fiber.

In case of a step refractive index, solutions are the Bessel functions of the first kind, $J_l(r)$, in the core region, and modified Bessel functions of the second kind, $K_l(r)$, in the cladding region.

In the case of step-index fiber the groups of modes are almost degenerate, also meaning that the polarization correction $\delta\beta$ can be considered very small. Unlike $HE_{11}$ modes, higher order modes (HOMs) can have elaborate polarizations. In the case of circularly symmetric fiber, the odd and even modes (for example $HE^{odd}$ and $HE^{even}$ modes) are always degenerate (i.e. have equal $n_{eff}$), regardless of the index profile. These modes will be non-degenerate only in the case of circularly asymmetric index profiles.

Figure 14:
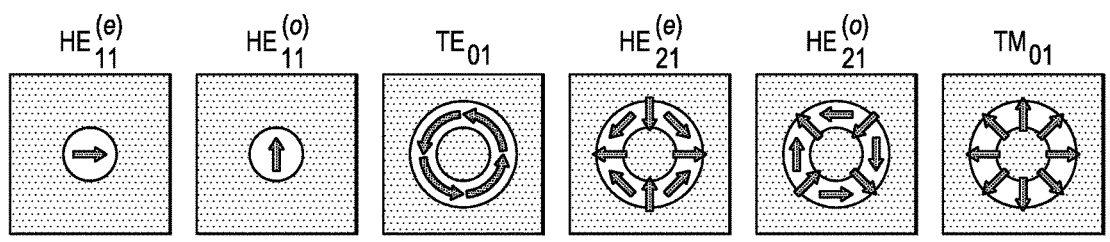
FIG. 14 illustrates the first six modes within a step-index fiber.

Referring now to FIG. 14, there are illustrated the first six modes within a step indexed fiber for the groups L=0 and L=1.

When orbital angular momentums are applied to the light wavelength within an optical transmitter of an optical fiber communication system, the various orbital angular momentums applied to the light wavelength may transmit information and be determined within the fiber mode.

Angular momentum density (M) of light in a medium is defined as:

$$M = \frac{1}{c^2}r \times (E \times H) = r \times P = \frac{1}{c^2}r \times S$$

with r as position, E electric field, H magnetic field, P linear momentum density and S Poynting vector.

The total angular momentum (J), and angular momentum flux ($\Phi_M$) can be defined as:

$$J = \iiint M \, dV$$

$$\Phi_M = \iint M \, dA$$

In order to verify whether certain mode has an OAM let us look at the time averages of the angular momentum flux $\Phi_M$:

$$\langle \Phi_M \rangle = \iint \langle M \rangle \, dA$$

as well as the time average of the energy flux:

$$\langle \phi_W \rangle = \iint \frac{\langle S_z \rangle}{c} dA$$

Because of the symmetry of radial and axial components about the fiber axis, we note that the integration in equation will leave only z-component of the angular momentum density non zero. Hence:

$$\langle M \rangle = \langle M \rangle_z = \frac{1}{c^2}r \times \langle E \times H \rangle_z$$

and knowing $\langle S \rangle = Re\{S\}$ and $S=\frac{1}{2}E \times H^*$ leads to:

$$S_\phi = \frac{1}{2}(-E_r H_z^* + E_z H_r^*)$$

$$S_z = \frac{1}{2}(E_x H_y^* - E_y H_x^*)$$

Let us now focus on a specific linear combination of the $HE_{l+1,m}^{even}$ and $HE_{l+1,m}^{odd}$ modes with $\pi/2$ phase shift among them:

$$V_{lm}^+ = HE_{l+1,m}^{even} + lE \, H_{l+1,m}^{odd}$$

The idea for this linear combination comes from observing azimuthal dependence of the $HE_{l+1,m}^{even}$ and $HE_{l+1,m}^{odd}$ modes comprising $\cos(\phi)$ and $\sin(\phi)$. If we denote the electric field of $HE_{l+1,m}^{even}$ and $HE_{l+1,m}^{odd}$ modes as $e_1$ and $e_2$, respectively, and similarly, denote their magnetic fields as $h_1$ and $h_2$, the expression for this new mode can be written as:

$$e=e_1+ie_2, \quad (2.35)$$

$$h=h_1+ih_2. \quad (2.36)$$

then we derive:

$$e_r = e^{i(l+1)\varphi} F_l(R)$$

$$h_z = e^{i(l+1)\varphi} n_{co} \left(\frac{\epsilon_0}{\mu_0}\right)^{\frac{1}{2}} \frac{(2\Delta)^{\frac{1}{2}}}{V} G_l^-$$

$$e_z = i e^{i(l+1)\varphi} \frac{(2\Delta)^{\frac{1}{2}}}{V} G_l^-$$

$$h_r = -i e^{i(l+1)\varphi} n_{co} \left(\frac{\epsilon_0}{\mu_0}\right)^{\frac{1}{2}} F_l(R)$$

Where $F_l(R)$ is the Bessel function and $$G_l^{\pm} = \frac{dF_l}{dR} \pm \frac{l}{R} F_l$$

We note that all the quantities have $e^{i(l+1)\phi}$ dependence that indicates these modes might have OAM, similarly to the free space case. Therefore the azimuthal and the longitudinal component of the Poynting vector are:

$$S_\varphi = -n_{co} \left(\frac{\epsilon_0}{\mu_0}\right)^{\frac{1}{2}} \frac{(2\Delta)^{\frac{1}{2}}}{V} Re\{F_l^* G_l^-\}$$

$$S_z = n_{co} \left(\frac{\epsilon_0}{\mu_0}\right)^{\frac{1}{2}} [F_l]^2$$

The ratio of the angular momentum flux to the energy flux therefore becomes:

$$\frac{\phi_M}{\phi_W} = \frac{l+1}{\omega}$$

We note that in the free-space case, this ratio is similar:

$$\frac{\phi_M}{\phi_W} = \frac{\sigma+1}{\omega}$$

where σ represents the polarization of the beam and is bounded to be −1<σ<1. In our case, it can be easily shown that SAM of the $V^+$ state, is 1, leading to important conclusion that the OAM of the $V^{+lm}$ state is 1. Hence, this shows that, in an ideal fiber, OAM mode exists.

Thus, since an orbital angular momentum (or other orthogonal function) mode may be detected within the ideal fiber, it is possible to encode information using this OAM mode in order to transmit different types of information having different orbital angular momentums within the same optical wavelength.

Figure 15:
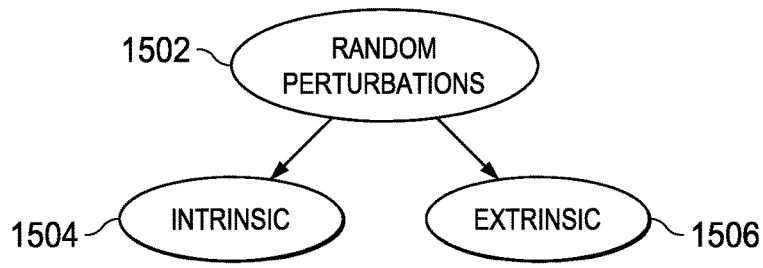
FIG. 15 illustrates the classes of random perturbations within a fiber.

The above description with respect to optical fiber assumed an ideal scenario of perfectly symmetrical fibers having no longitudinal changes within the fiber profile. Within real world fibers, random perturbations can induce coupling between spatial and/or polarization modes, causing propagating fields to evolve randomly through the fiber. The random perturbations can be divided into two classes, as illustrated in FIG. 15. Within the random perturbations 1502, the first class comprises extrinsic perturbations 1504.

Extrinsic perturbations 1504 include static and dynamic fluctuations throughout the longitudinal direction of the fiber, such as the density and concentration fluctuations natural to random glassy polymer materials that are included within fibers. The second class includes extrinsic variations 1506 such as microscopic random bends caused by stress, diameter variations, and fiber core defects such as microvoids, cracks, or dust particles.

Mode coupling can be described by field coupling modes which account for complex valued modal electric field amplitudes, or by power coupling modes, which is a simplified description that accounts only for real value modal powers. Early multimode fiber systems used incoherent light emitting diode sources and power coupling models were widely used to describe several properties including steady state, modal power distributions, and fiber impulse responses. While recent multimode fiber systems use coherent sources, power coupling modes are still used to describe effects such as reduced differential group delays and plastic multimode fibers.

By contrast, single mode fiber systems have been using laser sources. The study of random birefringence and mode coupling in single mode fibers which leads to polarization mode dispersion (PMD), uses field coupling modes which predict the existence of principal states of polarization (PSPs). PSPs are polarization states shown to undergo minimal dispersion and are used for optical compensation of polarization mode dispersion in direct detection single mode fiber systems. In recent years, field coupling modes have been applied to multimode fibers, predicting principal mode which are the basis for optical compensation of modal dispersion in direct detection multimode fiber systems.

Mode coupling can be classified as weak or strong, depending on whether the total system length of the optical fiber is comparable to, or much longer than, a length scale over which propagating fields remain correlated.

Figure 16:
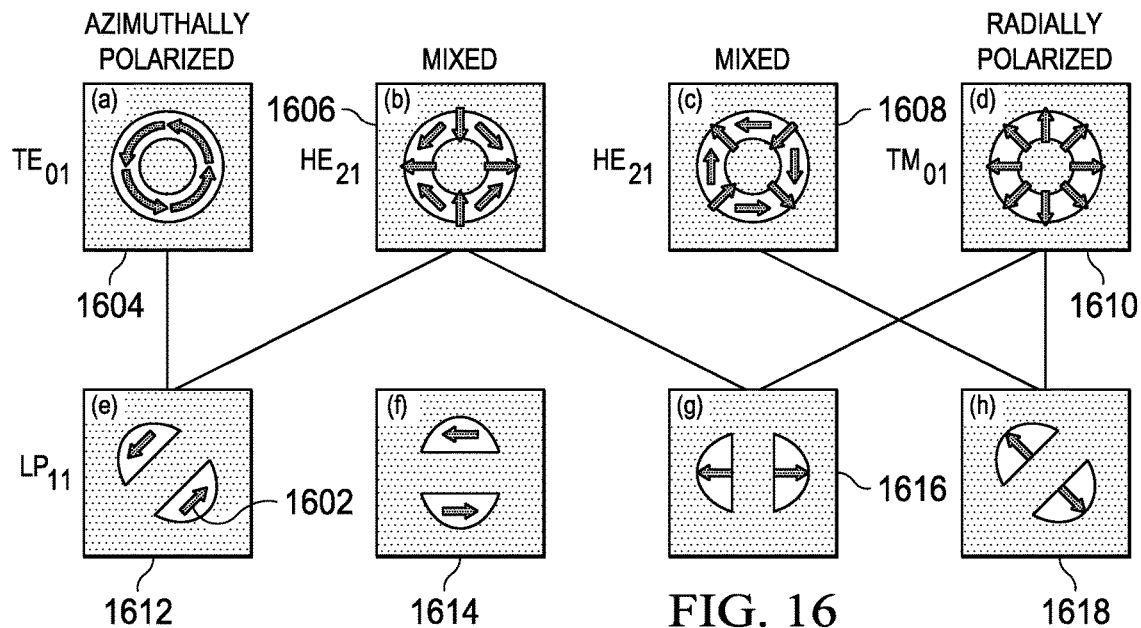
FIG. 16 illustrates the intensity patterns of first order groups within a vortex fiber.

Referring now to FIG. 16, there were illustrated the intensity patterns of the first order mode group within a vortex fiber. Arrows 1602 within the illustration show the polarization of the electric field within the fiber. The top row illustrates vector modes that are the exact vector solutions, and the bottom row shows the resultant, unstable LP11 modes commonly obtained at a fiber output. Specific linear combinations of pairs of top row modes resulting in the variety of LP11 modes obtained at the fiber output. Coupled mode 1602 is provided by the coupled pair of mode 1604 and 1606. Coupled mode 1604 is provided by the coupled pair of mode 1604 and mode 1608. Coupled mode 1616 is provided by the coupled pair of mode 1606 and mode 1610, and coupled mode 1618 is provided by the coupled pair of mode 1608 and mode 1610.

Typically, index separation of two polarizations and single mode fibers is on the order of 10-7. While this small separation lowers the PMD of the fiber, external perturbations can easily couple one mode into another, and indeed in a single mode fiber, arbitrary polarizations are typically observed at the output. Simple fiber polarization controller that uses stress induced birefringence can be used to achieve any desired polarization at the output of the fiber.

By the origin, mode coupling can be classified as distributed (caused by random perturbations in fibers), or discrete (caused at the modal couplers and the multiplexers). Most importantly, it has been shown that small, effective index separation among higher order modes is the main reason for mode coupling and mode instabilities. In particular, the distributed mode coupling has been shown to be inversely proportional to Δ-P with P greater than 4, depending on coupling conditions. Modes within one group are degenerate. For this reason, in most multimode fiber modes that are observed in the fiber output are in fact the linear combinations of vector modes and are linearly polarized states. Hence, optical angular momentum modes that are the linear combination of the HE even, odd modes cannot coexist in these fibers due to coupling to degenerate TE01 and TM01 states.

Thus, the combination of the various OAM (or other orthogonal function) modes is not likely to generate modal coupling within the optical systems and by increasing the number of OAM modes, the reduction in mode coupling is further benefited.

Figure 17:
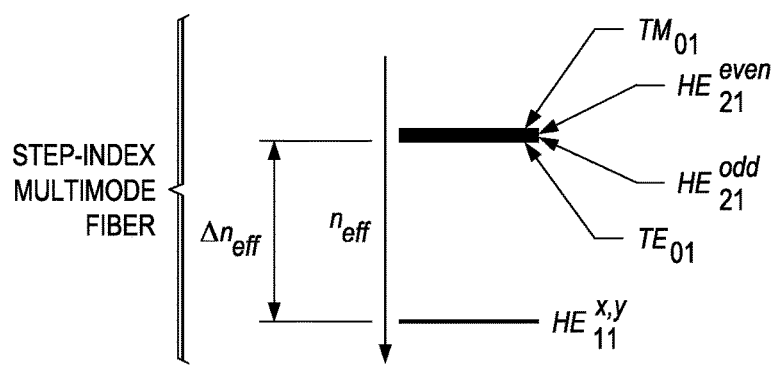
FIG. 17 illustrates index separation in first order modes of the multi-mode fibers.
Figure 18:
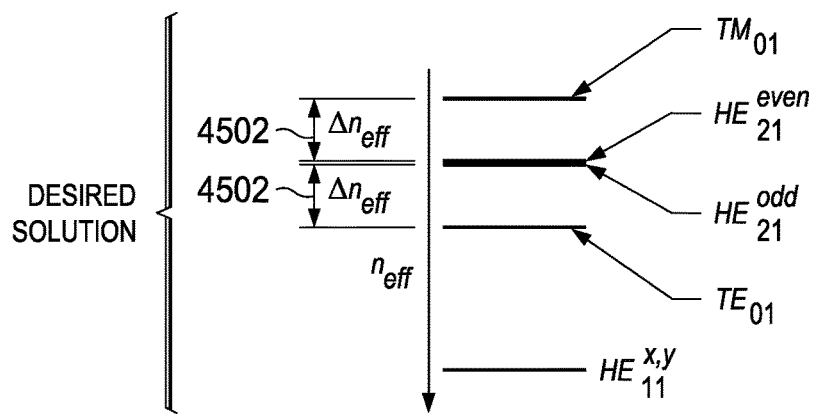
FIG. 18 illustrates index separation in first order modes of the multi-mode fibers.

Referring now to FIGS. 17 and 18, there is illustrated the benefit of effective index separation in first order modes. FIG. 17 illustrates a typical step index multimode fiber that does not exhibit effective index separation causing mode coupling. The mode $TM_{01}$ $HE^{even}_{21}$, mode $HE^{odd}_{21}$, and mode $TE_{01}$ have little effective index separation, and these modes would be coupled together. Mode $HE^{x,1}_{11}$ has an effective index separation such that this mode is not coupled with these other modes.

This can be compared with the same modes in FIG. 18. In this case, there is an effective separation 1802 between the $TM_{01}$ mode and the $HE^{even}_{21}$ mode and the $TE_{01}$ mode and the $HE^{odd}_{21}$ mode. This effective separation causes no mode coupling between these mode levels in a similar manner that was done in the same modes in FIG. 17.

In addition to effective index separation, mode coupling also depends on the strength of perturbation. An increase in the cladding diameter of an optical fiber can reduce the bend induced perturbations in the fiber. Special fiber design that includes the trench region can achieve so-called bend insensitivity, which is predominant in fiber to the home. Fiber design that demonstrates reduced bends and sensitivity of higher order Bessel modes for high power lasers have been demonstrated. Most important, a special fiber design can remove the degeneracy of the first order mode, thus reducing the mode coupling and enabling the OAM modes to propagate within these fibers.

Figure 19:
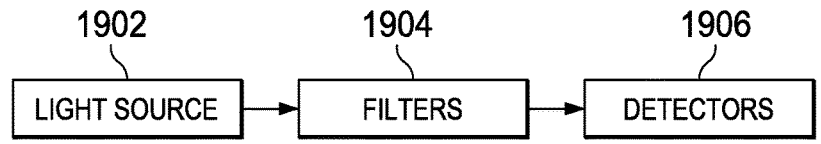
FIG. 19 illustrates a first implementation within the detector utilizing filters.
Figure 20:
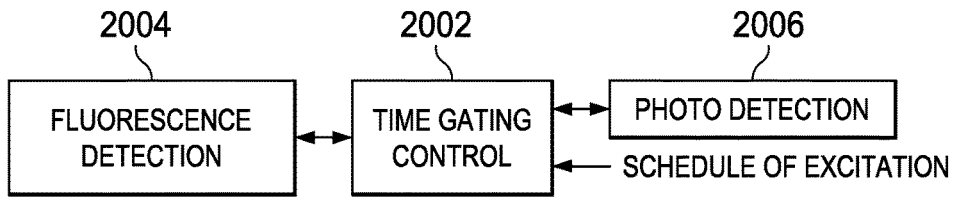
FIG. 20 illustrates a second implementation within the detector utilizing a time gating control.

The fluorescence detection subsystem 926 (FIG. 9) of the endoscope must be able to detect a weak fluorescent signal while rejecting stray light mostly from the video lamp illumination fibers 916. Two embodiments of detection methods are illustrated in FIGS. 19 and 20 can be used for the rejection of stray light. In the first method illustrated in FIG. 19, the light source 1902 is shined through optical filter 1904 before being provided to fluorescence detector 1906. The optical filters 1904 are used to block short wavelength components of the video lamp light source 1902 which can overlap with tissue fluorescence. This method is easy to implement and will be highly effective. However, this technique may give a video image a reddish tint since the filters 1904 will block part of the blue light spectrum. The reddish tint can be corrected by software.

A second method illustrated in FIG. 20 will use time-gating control 2002 to temporarily separate fluorescence measurements detection 2004 from the video lamp 2006. In this scheme, the time gating control 2002 pulls both the video and fluorescence light sources and the photo detection circuitry 2006 is gated. Fluorescence data can only be collected while the UV excitation source is on and the video lamp is off. Since the video is interlaced, the ultraviolet source can be pulsed at 60 Hz to give 60 fields per second (30 frames per second). The fluorescence excitation can be fired at twice the repetition rate of the video system to give increased fluorescence signals. Since the fluorescence lifetime is typically nanoseconds, and the light source pulse width is less than 10 μs for a xenon lamp or less than 10 nanoseconds for an LED. It is possible to pulse the fluorescence source at a frequency many times greater than the video system.

Figure 21:
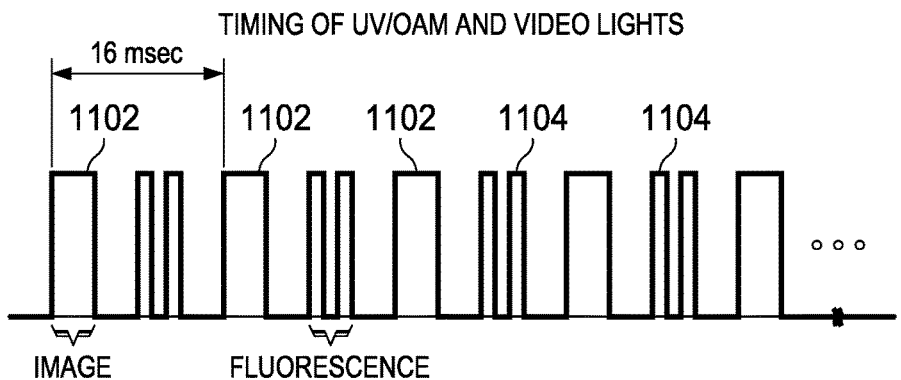
FIG. 21 illustrates the timing with respect to a ultraviolet/OAM and video light using a timing gating control.

Referring now to FIG. 21, there is illustrated the timing of the ultraviolet/OAM (or other orthogonal function) light source provided through excitation source 1012 and video light provided through the illumination source 1010. The video illumination lights provided by the illumination fiber 1010 and the ultraviolet OAM twisted light provided from the excitation fiber 1012 will not be provided at a same point in time. These lights will be timed such that one is provided and then the other using a timing scheme such as that illustrated in FIG. 21. As can be seen, the image light provided by the illumination fiber 1010 and the UV light provided from the image fiber 1008 are provided during differing time periods. The illumination pulses over the illumination fiber 1010 are provided at 16 ms intervals. An opening is provided between the illumination light pulses 1102. Within these openings, fluorescent light pulses 2104 are provided. The UV pulses have the fluorescent UV light OAM twists and are provided through the excitation fiber 920 between the video light pulses 1102.

Using the above described embodiment, improved detection of cancerous tissue using microendoscopes may be provided. While the present use of OAM (or other orthogonal function) twisted ultraviolet light within a ductoscopy/endoscopy procedure for use in examination of breast cancers has been primarily described herein, it will be appreciated that the endoscopy techniques and probes described herein may be utilized in other types of cancer detection systems within or on the exterior of the body and is not solely limited to the examination of breast cancer. Endoscopic probes for the examinations of other procedures would also be similarly configured.

It will be appreciated by those skilled in the art having the benefit of this disclosure that this orbital angular momentum (or other orthogonal function) and fluorescence-based microendoscope spectroscopy for cancer diagnosis provides improved cancer detection capabilities. It should be understood that the drawings and detailed description herein are to be regarded in an illustrative rather than a restrictive manner, and are not intended to be limiting to the particular forms and examples disclosed. On the contrary, included are any further modifications, changes, rearrangements, substitutions, alternatives, design choices, and embodiments apparent to those of ordinary skill in the art, without departing from the spirit and scope hereof, as defined by the following claims. Thus, it is intended that the following claims be interpreted to embrace all such further modifications, changes, rearrangements, substitutions, alternatives, design choices, and embodiments.

What is claimed is:

1. An apparatus for performing an endoscopic procedure for detecting cancerous tissue, comprising:
   a detection probe for detecting the cancerous tissue, the detection probe including a first fiber for emitting an ultraviolet light beam having an orthogonal function applied thereto and a second fiber for receiving emissions from tissues responsive to the ultraviolet light beam emitted for the first fiber;
   an ultraviolet emission source for generating the ultraviolet light beam;
   orthogonal function processing circuitry for applying the orthogonal function to the ultraviolet light beam; and detection circuitry for detecting fluorescence and orthogonal function within the emissions from the tissues received over the second fiber.

2. The apparatus of claim 1, wherein the ultraviolet emission source comprises:
a plurality of LEDs, each of the LEDs emitting ultraviolet light and a different wavelength; and
a switch for selecting between the plurality of LEDs responsive to a control input.

3. The apparatus of claim 1, wherein the detection probe further comprises:
a third fiber for providing images of tissues near the probe;
a scope connected to the third fiber for providing the images taken through the third fiber; and
a focusing mechanism for focusing an image being provided by the scope.

4. The apparatus of claim 3 further comprises:
at least one fourth fiber for providing an illumination beam for generating the images taken through the third fiber; and
a white light illumination source for generating the illumination beam.

5. The apparatus of claim 4 further including a timing control circuit for controlling illumination of the white light illumination source and the ultraviolet emission source, wherein white light illumination source and the ultraviolet emission source are controlled to be turned on at separate time periods.

6. The apparatus of claim 3 further comprising a photo detection circuit for generating the images of tissues responsive to information received over the third fiber.

7. The apparatus of claim 3 further comprising a photo detection circuit for generating the images of tissues responsive to information received over the third fiber.

8. The apparatus of claim 1 further including a filter for filtering white light from the detection circuitry.

9. The apparatus of claim 1 further including a display interface for generating a visual display of the information detected by the detection circuitry.

10. The apparatus of claim 1 wherein the detection circuitry compares the fluorescence and the orthogonal function within the emissions from the tissues with stored fluorescence and orthogonal function signatures of cancerous and non-cancerous tissues to detect the cancerous tissue.

11. The apparatus of claim 1 further including a filter for filtering white light from the detection circuitry.

12. The apparatus of claim 1 further including a display interface for generating a visual display of the information detected by the detection circuitry.

13. An method for detecting cancerous tissue using an endoscopic procedure, comprising:
generating the ultraviolet light beam;
applying an orthogonal function to the ultraviolet light beam;
applying the ultraviolet light beam having the orthogonal function applied thereto to tissue through a first optical fiber of a detection probe;
receiving a reflected ultraviolet light beam having the orthogonal function applied thereto from the tissue through a second fiber of the detection probe; and
detecting fluorescence and orthogonal function within the emissions from the tissues received over the second fiber.

14. The method of claim 13, wherein the step of generating comprises:
generating a plurality of ultraviolet light beams using a plurality of LEDs, each of the LEDs emitting a different wavelength; and
selecting between the plurality of ultraviolet light beams using a switch responsive to a control input.

15. The method of claim 13 further comprising:
taking images of the tissue using a scope through a third fiber in the detection probe; and
focusing an image being provided by the scope.

16. The method of claim 15 further comprises:
generating an illumination beam using a white light illumination source; and
providing the illumination beam for generating the images taken through the third fiber through a fourth fiber.

17. The method of claim 16 further including controlling illumination of the white light illumination source and the ultraviolet emission source to be turned on at separate time periods.

18. The method of claim 13 further including filtering white light from the detection circuitry.

19. The method of claim 13 further including generating a visual display of the information detected by the detection circuitry.

20. The method of claim 13 wherein the step of detecting further comprises comparing the fluorescence and the orthogonal function within the emissions from the tissues with stored fluorescence and orthogonal function signatures of cancerous and non-cancerous tissues to detect the cancerous tissue.

21. A detection probe for performing an endoscopic procedure for detecting cancerous tissue, comprising:
a first fiber for emitting an ultraviolet light beam having an orbital angular momentum twist applied thereto;
a second fiber for receiving emissions from tissues responsive to the ultraviolet light beam emitted for the first fiber;
a third fiber for providing images of tissues near the probe;
at least one fourth fiber for providing an illumination beam for generating the images taken through the third fiber;
a flexible sheet for enclosing the first fiber, the second fiber, the third fiber and the at least one fourth fiber.

22. The detection probe of claim 21 further including:
an ultraviolet emission source for generating the ultraviolet light beam;
orbital angular momentum circuitry for applying the orbital angular momentum twist to the ultraviolet light beam; and
detection circuitry for detecting fluorescence and orbital angular momentum within the emissions from the tissues received over the second fiber.

23. The detection probe of claim 22, wherein the ultraviolet emission source comprises:
a plurality of LEDs, each of the LEDs emitting ultraviolet light and a different wavelength; and
a switch for selecting between the plurality of LEDs responsive to a control input.

24. The detection probe of claim 22 wherein the detection circuitry compares the fluorescence and the orbital angular momentum within the emissions from the tissues with stored fluorescence and OAM signatures of cancerous and non-cancerous tissues to detect the cancerous tissue.

25. The detection probe of claim 21, wherein the detection probe further comprises:
a scope connected to the third fiber for providing the images taken through the third fiber; and
a focusing mechanism for focusing an image being provided by the scope.

26. The detection probe of claim 21 further including a timing control circuit for controlling illumination of the white light illumination source and the ultraviolet emission source, wherein white light illumination source and the ultraviolet emission source are controlled to be turned on at separate time periods.

27. The detection probe of claim 21 further including a filter for filtering white light from the detection circuitry.

28. An apparatus for performing an endoscopic procedure for detecting cancerous tissue, comprising:
 a detection probe for detecting the cancerous tissue, the detection probe including;
  a first fiber for emitting an ultraviolet light beam having an orbital angular momentum twist applied thereto;
  a second fiber for receiving emissions from tissues responsive to the ultraviolet light beam emitted for the first fiber;
  a third fiber for providing images of tissues near the probe;
  a scope connected to the third fiber for providing the images taken through the third fiber;
  at least one fourth fiber for providing an illumination beam for generating the images taken through the third fiber;
 an ultraviolet emission source for generating the ultraviolet light beam;
 a white light illumination source for generating the illumination beam;
 orbital angular momentum circuitry for applying the orbital angular momentum twist to the ultraviolet light beam;
 detection circuitry for detecting fluorescence and orbital angular momentum within the emissions from the tissues received over the second fiber, wherein the detection circuitry compares the fluorescence and the orbital angular momentum within the emissions from the tissues with stored fluorescence and OAM signatures of cancerous and non-cancerous tissues to detect the cancerous tissue.

29. The apparatus of claim 28, wherein the ultraviolet emission source comprises:
 a plurality of LEDs, each of the LEDs emitting ultraviolet light and a different wavelength; and
 a switch for selecting between the plurality of LEDs responsive to a control input.

30. The apparatus of claim 28 further including a timing control circuit for controlling illumination of the white light illumination source and the ultraviolet emission source, wherein white light illumination source and the ultraviolet emission source are controlled to be turned on at separate time periods.

* * * * *